United States Patent [19]

Crespi et al.

[11] Patent Number: 5,429,948
[45] Date of Patent: Jul. 4, 1995

[54] HUMAN CELL LINE STABLY EXPRESSING 5CDNAS ENCODING PROCARCINOGEN-ACTIVATING ENZYMES AND RELATED MUTAGENICITY ASSAYS

[75] Inventors: Charles L. Crespi, Marblehead; Bruce W. Penman, Salem, both of Mass.; Robin L. Davies, Amherst, Va.

[73] Assignee: Gentest Corporation, Woburn, Mass.

[21] Appl. No.: 997,455

[22] Filed: Dec. 28, 1992

Related U.S. Application Data

[63] Continuation-in-part of Ser. No. 597,815, Oct. 15, 1990, abandoned, and Ser. No. 771,520, Oct. 4, 1991, abandoned, which is a continuation of Ser. No. 162,885, Mar. 2, 1988, abandoned, said Ser. No. 597,815, is a continuation-in-part of Ser. No. 162,885, Mar. 2, 1988.

[51] Int. Cl.$^6$ ............................................. C12N 15/00
[52] U.S. Cl. .............................. 435/240.2; 435/172.1; 435/172.3
[58] Field of Search ..................................... 435/240.2

[56] References Cited

PUBLICATIONS

Daves et al Carcinogenes 10(S) 885, 1989.
Crespi et al Mutater & Environment, 97–106, 1990 Wiley–Tess, Inc.
Crespi et al Mol. Carcinogenes 3:58, 1990.
Crespi, C. et al., The development of human cell libes which stably express human cytochrome P450 cDNAs, Environmental and Molecular Mutagenesis, vol. 15, Suppl 17, 1990, p. 14 and 21st Annual Meeting of the Environmental Mutagen Society, Albuquerque N.Mex., Mar. 25–29, 1990, abstract No. 45.
Crespi, E. et al., A metabolically competent human cell line expressing five cDNAs encoding procarcinogen-activating enzymes: application to mutagenicity testing, Chemical Reaserch in Toxicity, vol. 4, No. 5, Sep. 1991, pp. 556–572.

Primary Examiner—Suzanne E. Ziska
Attorney, Agent, or Firm—Wolf, Greenfield & Sacks

[57] ABSTRACT

An immortal human cell line stably expressing a multiplicity of cytochrome P450s is provided. Preferably, the cell line is MCL-5, which stably expresses cytochrome P450 IA1, IA2, IIA3, IIIA4, and IIE1, as well as microsomal epoxide hydrolase. The cell line is useful in mutagenicity, toxicity and metabolism studies.

2 Claims, 16 Drawing Sheets

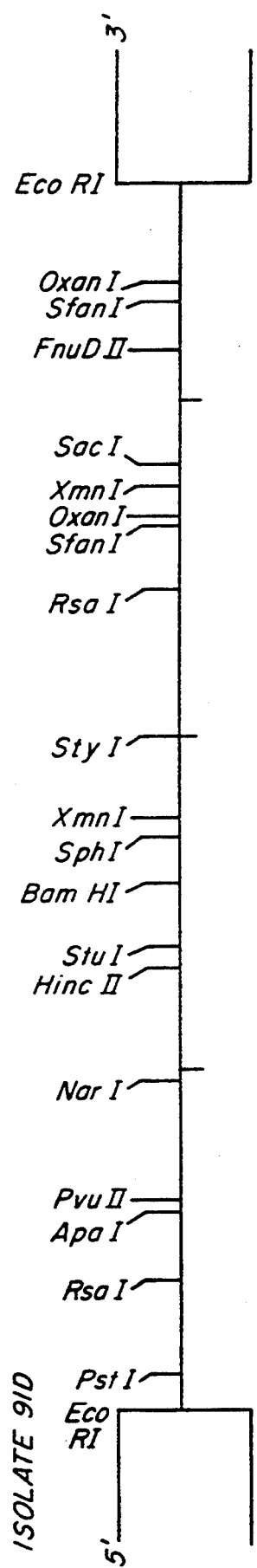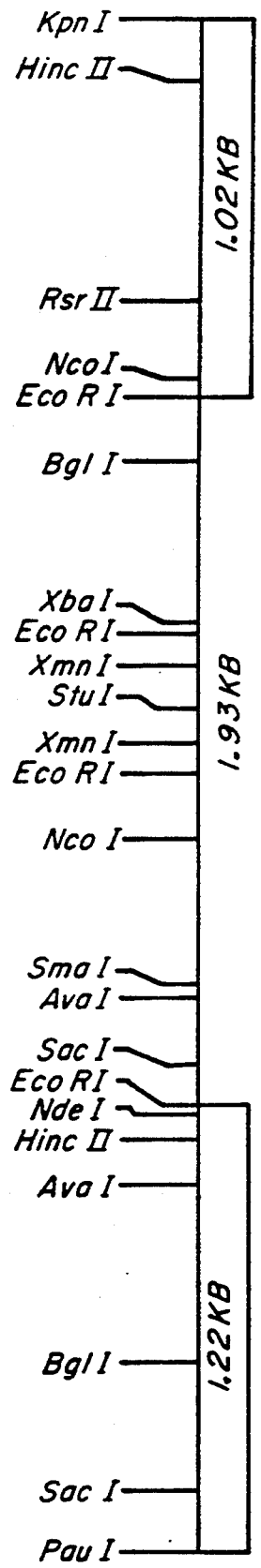

ENZYME EXPRESSION IN MCL-5 CELLS AND COMPARISON TO
EXPRESSION WITH A SINGLE cDNA PER VECTOR

| ASSAY | P450 FORM(S) | ENZYME ACTIVITY [PMOLE/($10^6$ CELLS x MIN)] TIME IN CULTURE | | | 1 cDNA/ VECTOR |
|---|---|---|---|---|---|
| | | 6 DAYS | 37 DAYS | 63 DAYS | |
| 7-ETHOXYRESORUFIN DEETHYLASE (BASAL) | IA1&IA2 | 0.40±0.02 | 0.40±0.01 | 0.27±0.02 | N/A |
| 7-ETHOXYRESORUFIN DEETHYLASE (INDUCED) | IA1&(IA2) | 1.71±0.13 | 1.68±0.05 | 1.35±0.07 | N/A |
| 7-ETHOXYRESORUFIN DEETHYLASE (INDUCED-BASAL) | IA1 | 1.32±0.11 | 1.29±0.04 | 1.09±0.09 | N/A |
| ACETANILIDE 4-HYDROXYLASE | IA2 | 1.40±0.06 | 1.52±0.11 | 1.36±0.11 | 1.2 (28) |
| COUMARIN 7-HYDROXYLASE | IIA2 | 1.02±0.11 | 1.82±0.08 | 1.59±0.18 | 1 (8) |
| CHLORZOXAZONE-6-HYDROXYLASE | IIE1&(IA2) | 1.47±0 | 1.52 | 1.18±0.28 | 0.5* |
| TESTOSTERONE 6β-HYDROXYLASE | IIIA4 | 0.98±0.04 | 0.97±0.08 | 1.22±0.12 | 1.4 (28) |
| BENZO(A)PYRENE-(4,5)-OXIDE HYDROXYLASE | mEH | 1.04±0.08 | 1.14±0.07 | 1.24±0.11 | 1.8 (6) |
| N-NITROSODIMETH-YLAMINE CYTOTOX-ICITY (100ng/ml) | IIE1&(IIA2) | S=0.13±0.03 | S=0.11±0.01 | S=0.10±0.02 | |

VALUES ARE THE MEAN ± STANDARD DEVIATION FOR TWO INDEPENDANT CULTURES.

* UNPUBLISHED OBSERVATION.

FIG. 9

COMPARISON OF THE SENSITIVITIES OF MCL-5 CELLS AND
THE PARENT AHH-1 tk +/- CELL LINE

| CARCINOGEN | CALCULATED CONCENTRATION NECESSARY TO DOUBLE THE MUTANT FRACTION | | FOLD INCREASE IN SENSITIVITY |
|---|---|---|---|
| | MCL-5 | AHH-1 tk+/- | |
| BENZO(A)PYRENE | 1.2 ng/ml | 1,000 ng/ml (8) | 830 |
| 3-METHYLCHLORANTHRENE | 4.4 ng/ml | NOT DONE | |
| N-NITROSODIETHYLAMINE | 13 ng/ml | > 100,000 ng/ml (8) | > 7,700 |
| N-NITROSODIMETHYLAMINE | 5 ng/ml | > 200,000 ng/ml (8) | > 40,000 |
| AFLATOXIN $B_1$ | 0.6 ng/ml | 1,000 ng/ml (8) | 1,700 |
| 2-ACETOAMINOFLUORENE | 8,000 ng/ml | 2,500 ng/ml (5) | 3.1 |
| BENZIDINE | 86,000 ng/ml | 70,000 ng/ml (*) | 0.8 |

\* UNPUBLISHED OBSERVATIONS

FIG. 12

HUMAN CELL LINE STABLY EXPRESSING 5CDNAS ENCODING PROCARCINOGEN-ACTIVATING ENZYMES AND RELATED MUTAGENICITY ASSAYS

GOVERNMENT SUPPORT

Work relating to this invention was supported in part by a contract from the National Institute of Environmental Health Sciences.

RELATED APPLICATIONS

This application is a continuation in part of U.S. application Ser. No. 07/597,815, filed Oct. 15, 1990, now abandoned which was a continuation in part of U.S. application Ser. No. 07/162,885, filed Mar. 2, 1988 (now abandoned). This application is also a continuation in part of U.S. application Ser. No. 07/771,520, filed Oct. 4, 1991, now abandoned which was a continuation of U.S. application Ser. No. 07/162,885, filed Mar. 2, 1988now abandoned.

FIELD OF THE INVENTION

This invention relates in general to the fields of biochemistry, molecular biology, pharmacology and toxicology, and specifically to a genetically engineered cell line useful in mutagenicity, toxicity and metabolism studies.

BACKGROUND OF THE INVENTION

Human beings suffer serious health risks when exposed to certain chemical substances. Among these risks is the effect of genetic alteration caused by chemically-induced mutation. The results of such genetic alteration can be devastating, as for example, when the mutation is to the DNA of a gamete contributing critical genetic information to a developing embryo. Also, chemically-induced mutation in somatic cells may be a contributing cause to many cancers.

Investigators have developed mutagenicity assays that measure the ability of chemical agents or physical agents such as an X-ray to cause an alteration in the DNA of an organism. Such assays may be used to predict the carcinogenic potential of the agent on the basis of its ability to induce mutations in cultured cells.

Mutagenicity assays typically involve exposing a cell culture to an agent. After exposure is terminated, the culture is allowed to grow for a period of time necessary to allow a mutant phenotype to be expressed. The frequency of the mutant phenotype in the test culture then is compared to a control culture to determine whether exposure induced a higher frequency of mutation.

A useful characteristic which may be used to determine the occurrence of a mutation is a cell's ability to make an enzyme after exposure to a potential mutagen. A cell may possess an enzyme that will convert a non-toxic substance into a toxin. Such cells will die when grown in the presence of the non-toxic precursor. A mutation to a gene related to the enzyme may eliminate the enzyme as a product of the cell. Such a mutated cell not producing the enzyme will live when grown in the presence of the non-toxic precursor because it will not have the ability to convert the non-toxic precursor into a toxin. Thus, the existence of the mutation may be determined by the ability of a cell to grow in media containing the non-toxic precursor.

Mutation assays have been performed using a number of precursors of this nature, including the following: 6-thioguanine (6-TG), which kills cells that contain hypoxanthine-guanine-phosphoriboxyl transferase (HGPRT)[1]; 8-azaguanine, which kills cells that contain HGRPT [2]; and trifluorodeoxythymidine, which kills cells that contain thymidine kinase [3].

Cells from various organisms have been used in mutagenicity assays, including cells from bacteria [4, 5] yeast [6], hamsters [7, 8], mice [9] and humans [10, 11, 12, 13]. However, species differ in their sensitivity to various substances. Thus, data from assay systems incorporating human cells should be most predictive of potential effects in human populations.

A considerable body of evidence indicates that it is the metabolites of many xenobiotics which are ultimately responsible for the mutagenic effect rather than the xenobiotic compounds themselves. However, cell lines grown in long-term cell culture tend to lose their ability to metabolize xenobiotics and therefore cannot be used to accurately predict the potential carcinogenicity of a substance. To overcome this problem, an exogenous source of xenobiotic metabolism has been provided in various mutagenicity assays.

Two general approaches have been taken to provide xenobiotic metabolism in in vitro mutagenicity assays. The most common approach is to use a homogenate of a tissue rich in the enzymes responsible for the metabolism of xenobiotics, usually rat liver [14, 15]. However, such exogenous homogenates are unsatisfactory because they come from rats, not humans, and because they are known to metabolize chemicals differently than the intact tissue [16]. Furthermore, the use of exogenous homogenates complicates the procedure by requiring additional steps, including careful control of pH and sterility. Moreover, the addition of such homogenates creates conditions different from those existing normally in vivo.

Another approach is to co-cultivate metabolically-competent cells with the suitable target cells [17, 18]. This approach, however, requires unstable, chemically-reactive metabolites to traverse from the metabolically-competent cells to the DNA of the target cells, with a concomitant loss of sensitivity.

One recent improvement to the foregoing mutagenicity assay systems is described in U.S. Pat. No. 4,532,204, the disclosure of which is incorporated by reference. This patent describes a newly-isolated and purified human cell line, designated as AHH-1 cells. The AHH-1 cell line is described as being isolated from a culture of lymphoblast cells supplied by the Roswell Park Memorial Institute (RPMI-1788 cells). The cell line was selected to have: rapid growth rate and high cloning efficiency; the absence of mycoplasma; the ability to grow in suspension; and a stable near diploid genome. In addition, the AHH-1 cell line was selected to have high levels of oxidative activity, as compared to the RPMI-1788 cells and in particular high aryl hydrocarbon hydroxylase (AHH) activity. This activity is due primarily to the cytochrome P450IA1 (for the purposes of this document we employ the Cytochrome P450 nomenclature described in Nebert et al, 1987 DNA 6:1–11) mono-oxygenase responsible for converting certain xenobiotic compounds into mutagenic metabolites. Thus, it was stated that the AHH-1 cell line does not require an exogenous source of cytochrome P450IA1 for mutagenicity studies.

At least four characteristics of AHH-1 cells limit their usefulness in mutagenicity assays and metabolic transformation studies:

(1) The induction of gene mutations can only be measured at the hemi-zygous (X-linked) HGPRT locus; however, recovery of induced mutants may be much higher at autosomal loci.

(2) The level of cytochrome P450IA1 activity in AHH-1 cells, while sufficient to activate some chemicals to their mutagenic form, is unacceptably low for other chemicals. Therefore, the mutagenicity of certain chemicals inefficiently acted on by cytochrome P450IA1 will go undetected in a mutagenicity assay using AHH-1 cells.

(3) AHH-1 cells do not detectably express cytochrome P450 mono-oxygenase of the P450II class. Members of this class convert certain substances such as nitrosamines, into mutagenic metabolites which are of considerable concern to human health. AHH-1 cells are relatively insensitive to the mutagenic effects of nitrosamines and, therefore, AHH-1 cells will not detect the mutagenic effect of this important class of compounds.

(4) AHH-1 cells do not express detectable levels of microsomal epoxide hydrolase (E.C. 3.3.2.3) and thus do not produce the known mutagenic metabolites of polycyclic aromatic hydrocarbons that are found in vivo.

The AHH-1 cell line does not have the oxidative activity found in vivo and responsible for the metabolism of considerably large classes of xenobiotics into mutagenic end products. A human cell line stably expressing the genes responsible for this oxidative activity would be very desirable. One group recently has reported the transfer of mouse cytochrome P-450 genes into mouse and human cells using a viral vector [19]. These genes were expressed in both populations of cells infected with the recombinant virus for up to ten hours after infection. Mutagenicity and other toxicological assays, however, require stable and homogenous expression of metabolizing enzymes which was not demonstrated in that study.

The cytochromes P450 are a large family of hemoproteins capable of metabolizing xenobiotics such as drugs, procarcinogens and environmental pollutants as well as endobiotics such as steroids, fatty acids and prostaglandins. Many mammalian cell lines have lost most or all capacity to perform cytochrome P450-catalyzed reactions. This limitation has restricted studies of cytochrome P450 mediated metabolism to either primary cells or tissue homogenates. The lack of adequate endogenous cytochrome P450's has also led to the incorporation of extracellular metabolizing systems, commonly rodent liver homogenates, into assays designed to detect genotoxic effects of promutagens and procarcinogens.

Recently, several laboratories have successfully transfected cytochrome P450 cDNAs into mammalian cell lines. Virtually all of the cell lines were developed by transfecting a single P450 cDNA into the target cell line. While these cell lines may be quite useful for examining P450 specific activation of procarcinogens, given the multiplicity of P450 forms expressed in vivo, it is clear that the use of cell lines expressing single P450s to screen compounds for mutagenic activity will be a daunting task because of the number of cell lines needed. Accordingly, it would be desirable to utilize a small number of cell lines expressing a multiplicity of P450s. It would be even more desirable to have and utilize a single cell line stably expressing the all of the human P450 forms primarily responsible for the activation of procarcinogens in human microsomes.

The task of creating a cell line stably expressing a multiplicity of P450s has clear obstacles. Because the P450 genes have substantial homology, it would be expected that a single cell line transfected with multiple P450s would be unstable due to the likelihood of inter or intra vector recombination. Additionally, instability further would be expected in a cell-line containing multiple transfected promoters due to the promoters interfering with one another. These and other obstacles are overcome by the methods and cell lines of the invention.

SUMMARY OF THE INVENTION

According to the invention, a cell line expressing a multiplicity of P450s is provided, as well as methods for creating such cell lines and uses for such cell lines.

According to one aspect of the invention, an immortal mammalian cell line is provided which is capable of stably expressing at least two, different, transfected cytochrome P450s at levels below that which renders P450 expression in the cell line unstable. Preferably, at least one of the P450s is IA2 or IIA2, and more preferably the cell line expresses IA2, IIE1 and IIIA4. A preferred embodiment of the invention consists of the human lymphoblastoid cell line MCL-1. MCL-1 cells stably express both a human cytochrome P450IA1 and cytochrome P450IIA2 mixed function oxygenase. MCL-1 cells also express human epoxide hydrolase. The MCL-1 cell line is heterozygous for thymidine kinase which allows measurement of induced mutation at autosomal loci via resistance to pyrimidine analogues such as trifluorothymidine. The MCL-1 cell line also possesses other characteristics such as high plating efficiency in microtiter plates and rapid growth in suspension culture which enhances its usefulness in mutagenicity assays and metabolic transformation studies. In addition to the MCL-1 cell line, the invention includes mutants or variants of this cell line that express P450IA1, P450IIA2, and epoxide hydolase. The MCL-1 cell line is deposited at ATCC and has ATCC accession number CRL9652.

The most preferred embodiment of the invention is a human lymphoblastoid cell line MCL-5. MCL-5 cells stably express IA2, IIA2, IIIA4 and IIE1, as well as IA1 and human epoxide hydrolase. The MCL-5 cell line was deposited on Oct. 12, 1990 at ATCC Rockfield, Md., and has ATCC accession no. CRL 10575. In addition to this cell line, mutants, derivations, variants or modifications of the preferred embodiments may be made. For example, other human cell lines or mammalian cell lines may be used to receive the recombinant expression vectors of the invention, so that the modified cell line expresses at least two different, transfected P450s.

According to another aspect of the invention, a method for regulating the relative expression of two cDNAs is provided. According to this method, the efficiency of expression of at least two different cDNAs is matched with the number of copies of the cDNAs introduced into the cell line. For example, an inefficiently expressed cDNA is introduced into a cell line on a nonintegrating vector at a relatively high copy and an efficiently expressing cDNA in a nonintegrating vector is introduced into the cell line at a relatively low copy.

In this manner, relative expression of the two cDNAs is regulated. Alternatively, an efficiently expressed cDNA is introduced into a cell line on a nonintegrating vector at a relatively high copy and an inefficiently expressing cDNA in a nonintegrating vector is introduced into the cell line at a relatively low copy. These methods may be employed, for example, to model a specific tissue having these criteria for expression of the genomic, corresponding DNA.

According to another aspect of the invention, a method and cell lines for modeling an in vivo metabolic pathway are provided. At least three, different cDNAs are transfected into an immortal cell line, the expression of which cDNAs together are required for reproducing in vitro the in vivo metabolic pathway.

According to still another aspect of the invention, an improvement to a method for conducting a metabolism, toxicity or mutagenicity assay is provided. The improvement is characterized by using a cell line stably expressing at least two, different, transfected cytochrome P450s at levels below that which renders P450 expression in the cell line unstable.

BRIEF DESCRIPTION OF THE DRAWINGS

FIG. 1 is a restriction endonuclease map of a fragment of human DNA including the gene encoding P450IIA2. There are no cuts by Acc I, Ava I, Bgl I, Bgl II, Cla I, Dra I, Hind III, Kpn I, Pvu I, Sal I, Sma I, Xba I and Xho I.

FIG. 2 is a restriction endonuclease map of a fragment of human DNA including the gene encoding human epoxide hydrolase. There are no cuts by Acc I, Apa I, Bsm I, Cla I, Dra I, Hinc II, Hind III, Kpn I, Nae I, Nar I, Nde I, Nhe I, Not I, OxaN I, Pvu I, Rsr II, Sal I, Tth 111 I, Xho I.

FIG. 9 is a table of the enzyme expression levels in the MCL-5 cell line compared to expression in cells having a single cDNA per vector.

FIG. 12 is a table of the sensitivities of the MCL-5 cell line and AHH-1 cells to the mutagenic effects of benzo(a)pyrene, 3-methylchloranthrene, N-nitrosodiethylamine, N-nitrosodimethylamine, aflatoxin $B_1$, 2-acetoaminofluorene and benzidine.

DETAILED DESCRIPTION OF THE PREFERRED EMBODIMENT

Figure 3:
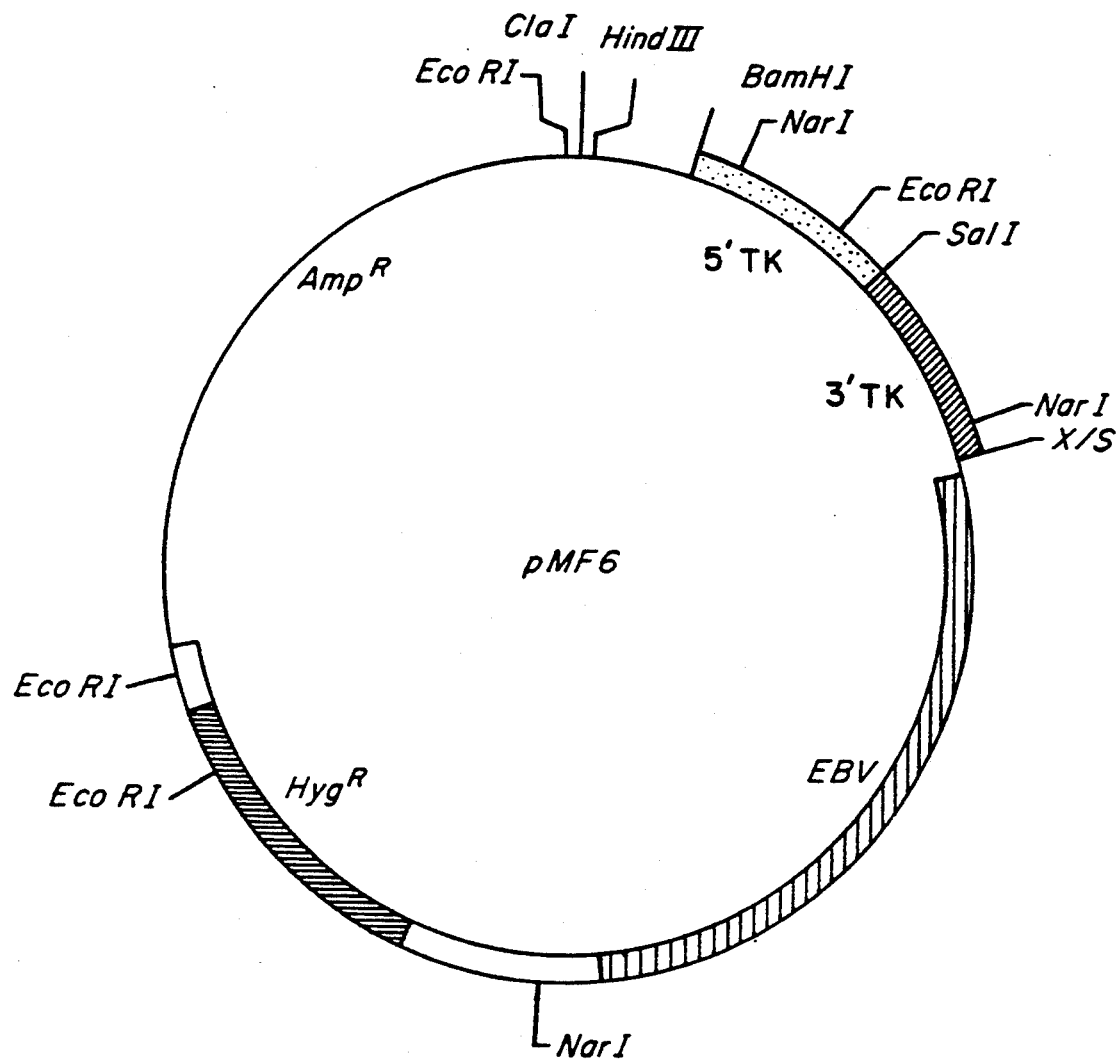
FIG. 3 is a restriction endonuclease map of the recombinant expression vector pMF6.

A cell line expressing a multiplicity of P450s is provided according to the invention. MCL-1 cells were derived ultimately from the AHH-1 cell line [13,20], ATCC accession number CRL8146. These cells were chosen because they expressed some level of P450IA1 activity, grew well in suspension culture, had an infinite life span and had the ability to form colonies in microtiter plates. AHH-1 cells also were found to have a near diploid chromosome number of 49, including one minute chromosome. It will become apparent from the following description that immortal human cell lines other than AHH-1 could be substituted for AHH-1 according to various embodiments of the invention.

The preferred cell line, MCL-5, expresses P450IA2, P450IIA2, P450IIE1, and P450IIIA4, which P450s are those primarily responsible for the activation of the major known procarcinogens. It also expresses P450 IA1, as well as epoxide hydrolase. The cell line thus may be used as a screening tool and avoids the need of using numerous separate cell lines as well as numerous separate assays for screening the known major procarcinogens.

The nomenclature of the cytochrome p450s has changed since the filing of U.S. patent application Ser. No. 07/162,885 upon which priority is claimed. The cytochrome P450 IIA2 referred to in U.S. patent application Ser. No. 07/162,885 was referred to as cytochrome P450 IIA3 at the time of filing U.S. patent application Ser. No. 07/597,815. Cytochrome P450 IIA3 currently is referred to as cytochrome P450 2A6.

Surprisingly, it was discovered that when P450 expression reaches a certain level (1 pmole/$10^6$ cells for the cell line employed), P450 expression becomes unstable. By unstable it is meant that the activities of the cDNA expressed enzymes change as a function of time of cell growth in culture. Therefore, not only was it necessary to engineer multiple P450s into a single cell line, but it was further necessary to do so in a manner so as to regulate the absolute expression of P450 in the cell and avoid cell shutdown of P450 production. It was anticipated that the use of multiple promoters controlling multiple cDNAs would result in promoter interference and unpredictable or unacceptable expression levels. Likewise, it was anticipated that the relatively high degree of homology between the P450 cDNAs, as well as between their respective promoters, would result in a reduction or loss of expression through recombination. It was also desirable, if not critical, to create a transfection scheme that did not require five separate transfections and five different selectable markers, one each for each transfected cDNA.

Thus, according to the invention, two approaches were simultaneously employed. First, multiple cDNAs were incorporated into single, non-integrating vectors. Second, high expressing cDNAs were incorporated into cell lines at low copy number, whereas relatively low expression cDNAs were incorporated into cell lines at relatively high copy numbers. In this manner, adequate expression of the various P450s was achieved, while maintaining the absolute expression of P450 at a level lower than that which would result in unstable expression of P450s. In the particular cell line used, that level was 1 pmole/$10^6$ cells. However, it will be understood that the level will vary depending upon the particular cell line chosen, and the invention is not limited to levels of expression below that value. Rather, the invention is intended to encompass cell lines expressing a multiplicity of P450s at levels below that which renders expression unstable, regardless of what the particular, absolute level for a particular cell line may be.

The cell lines according to the invention may be used in mutagenicity assays. For example, a culture of MCL-5 cells is exposed to a substance. Then the exposed cells are grown for a period of time sufficient to allow phenotypic expression. Next, the mutant frequency is determined. Finally, the frequency of mutation of the exposed cells is compared to the frequency of mutation of unexposed cells of the same type to determine the mutagenicity of the substance.

The cell lines may be used in metabolism studies. For example, a culture of MCL-5 cells or an enzyme preparation made from MCL-5 cells are incubated with a test substance. After a period of time the metabolite(s) and unmetabolized test substance are separated, if necessary. Methods of separation may include but are not limited to, solvent extraction, high performance liquid chromatography (HPLC) and other chromatographic separations. The amount of metabolite(s) then is quantified by measuring some physical characteristic of the metabolite(s). Such measurements may include, but are not limited to, absorbance of light, fluorescence and liquid scintillation counting.

The cell lines of the invention also may be used in toxicity assays. For example, a culture of MCL-5 cells is exposed to a substance. Next, the increase in cell number is determined over a period of time. Finally, the increase in cell number of exposed cells is compared to the increase in cell number of unexposed cells to determine the toxicity of the substance. Alternatively, the colony forming ability of exposed cells is compared to the colony forming ability of unexposed cells to determine the toxicity of the substance.

MCL-5 cells were derived from the L3 cell line, a variant of the AHH-1 human B lymhoblastoid cell. Construction of the L3 cell line was described in pending U.S. application Ser. No. 07/162,885, incorporated in its entirety herein by reference. The referenced procedure for construction of the L3 cell line is described in detail below. Construction of the parent AHH-1 cell line was described in U.S. Pat. No. 4,532,204, also is incorporated in its entirety herein by reference. Like the parent cell line, these cells express an enhanced level of P450IA1 activity, grow well in suspension culture, have an infinite life span and have the ability to form colonies in microtiter plates. Unlike the parent cell line, the MCL-5 cells were found to be more sensitive to the cytotoxicity of benzo(a)pyrene, 3-methylchloranthene, N-nitrosodiethylamine, N-nitrosodimethylamine, aflatoxin $B_1$ and 2-acetoaminofluorene.

For all procarcinogens except Benzidine, the MCL-5 cell line was significantly more sensitive than AHH-1 cells. The nitrosamines were more than 10,000 fold more active, Benzo(a)pyrene and Aflatoxin $B_1$ were about 1000 fold more active and 2-Acetoaminofluorene was 3 fold more active in MCL-5 cells. Only Benzidine gave comparable responses in both cell lines. Based on the mutagenic responses observed in MCL-5 cells and the comparisons to AHH1 cells, we conclude that we have substantially improved the procarcinogen activating capacity by the transfection procedure. MCL-5 cells were very sensitive to the mutagenic effects of two polycyclic aromatic hydrocarbons, two nitrosamines, a mycotoxin and an aromatic amide. These results indicate that this cell line can activate a spectrum of procarcinogens.

It will become apparent from the following description that immortal human cell lines other than those ultimately derived from AHH-1 could be substituted for the L3 cell line according to various embodiments of the invention.

Materials and General Procedures

RPMI medium 1640 was obtained from Sigma Chemical Company, St. Louis, Mo. or Hazelton, Inc., Denver, Pa. Horse serum was obtained from Hazelton, Inc. Cells were propagated in a normal growth medium of RPMI medium 1640 supplemented with 9% v/v horse serum. Cells were cultured in polystyrene tissue culture flasks. Routine cell culturing was performed by determination of cell number by electronic particle counting and diluting the cells with fresh medium to 3 or $4 \times 10^5$ cells per ml every day, $2 \times 10^5$ cells per ml every two days or $1 \times 10^5$ cells per ml every 3 days. Centrifugations of human lymphoblasts were performed at $1000 \times g$ for 5 minutes. Cells bearing recombinant plasmids were maintained in either medium containing 100–200 ug/ml hydromycin B (for pMF6-based vectors) or in medium containing 2 mM 1-histidinol, without 1-histidine (for pEBVHistk-based vectors). Protoplast fusions were performed according to published procedures [20]. Plating of the cells was performed in 96 well microtiter plates according to the technique of Furth et al, 1981 [21]. Plates were incubated for 13 days to allow colony formation. Hygromycin B was obtained from Calbiochem, La Jolla, Calif. Unlabeled and [$^3$H]-benzo(a)pyrene-4,5-oxide were obtained from the National Cancer Institute Chemical Carcinogen Repository. 6-(beta)-hydroxytestosterone standard was obtained from Steraloids, Inc., Wilton, N.H. 6-hydroxychlorzoxaxone standard was a gift of Dr. F. P. Guengerich, Vanderbilt University, Nashville. All other chemicals were obtained from Sigma Chemical Company, St. Louis, Mo.

Construction of the L3 Cell Line:

Isolation of Cells Containing Higher Levels of P450IA1Activity

An AHH-1 tk± derivative containing higher levels of the native P450IA1 activity was isolated from a mutagen-treated population using resistance to the phototoxicity of benzo(ghi)perylene (B(ghi)P). Near UV light is highly toxic to cells which have been exposed to small (0.1–0.2 uM) quantities of the photosensitizing agent benzo(ghi)perylene. Cells which can metabolize benzo(ghi)perylene (express P450IA1 activity) are markedly less sensitive to this toxicity. This property was utilized to isolate a rare variant of AHH-1 tk± which expresses substantially higher levels of P450IA1.

The B(ghi)P selection procedure was as follows. Human lymphoblastoid cells ($5 \times 10^5$ cells per ml in either 50 ml or 100 ml total volume as indicated) in normal growth medium were incubated at 37° C. for 2 hours in the presence of 0.2 or 0.4 uM B(ghi)P (as indicated). Dimethylsulfoxide was the solvent for B(ghi)P and the final solvent concentration was 0.1%. Cells were then centrifuged, resuspended in RPMI medium 1640 without serum supplement and incubated at 37° C. for 4 hours. Cells were exposed to 10 kilojoules near ultraviolet light (1 hour at room temperature) and horse serum (10% v/v) was added back to the culture. Cell growth was monitored after treatment by determing cell concentration every 1 to 3 days. After recovery, cells were diluted as described in the general procedures.

AHH-1 tk± cells (50 ml at $4 \times 10^5$ cells per ml) were exposed to ICR-191 for 1 day to attempt to create a mutant with higher levels of expression of P450IA1. Cells were centrifuged, resuspended in fresh medium and grown for 7 days maintaining at least $2 \times 10^7$ cells during all passaging. Cultures were subjected to 5 sequential selections with 0.2 uM B(ghi)P (the culture volume was 100 ml for the first two selections and 50 ml thereafter). The time required for the cell populations to recover from the toxicity associated with the B(ghi)P selection decreased from 11 days to 2 days during the sequential treatments indicating the selection of a more resistant population. The cell population was then given 4 additional sequential treatments with 0.4 uM B(ghi)P (the culture volume was 50 ml for all four) to provide an additional level of selection. Colonies derived from single cells were isolated by plating the cells at 0.2 cells per well. Six colonies were expanded to bulk populations and were screened for sensitivity to the cell growth inhibiting effects of benzo(a)pyrene, aflatoxin-$B_1$ dimethylnitrosamine, fluoranthene, cyclophosphamide and safrole. One colony, designated L3, was found to be more sensitive to the cytotoxicity of benzo(a)pyrene and aflatoxin-$B_1$. This isolate was found to metabolize benzo(a)pyrene 2 to 3 times more efficiently than AHH-1 tk± cells (example 11) and to be more sensitive to benzo(a)pyrene induced mutation at the hgprt locus (example 11). L3 cells were also found to have a lower background at the tk locus than the parent AHH-1 tk± cells ($5 \times 10^6$ for L3 cells versus $15 \times 10^6$ for AHH-1 tk± cells).

Libraries and plasmids.

A rat liver cDNA library (RL1001b), a human liver cDNA library (HL1001b) and a human placenta cDNA library (HL1008) were obtained from Clontech, Palo Alto, Calif. All three libraries were constructed in bacteriophage lambda gt11 [22] and were propagated in E. coli Y1090 [23].

Plasmid pHEBo [24] was obtained from Dr. William Sugden, University of Wisconsin, Madison. The vector pHEBo bears the genes for ampicillin resistance and hygromycin resistance, and contains sequences from the origins of replication of the Epstein-Barr virus and pBR322 which allow it to replicate autonomously in both EBV-transformed lymphoblastoid cells and E. coli [24]. pHEBo is 7.1 kb in size and possesses unique sites for the restriction enzymes Cla I, Hind III, Bam HI and Sal I, which may be used for the insertion of the DNA of interest.

Plasmid pHSV106 was purchased from Bethesda Research Laboratories, Gaithersburg, Md. The vector pHSV106 bears the herpes simplex virus thymidine kinase gene (HSV tk gene) and was used as a source for the control sequences of the HSV tk gene. All plasmids were propagated in E. coli HB101 [25].

The construction of the pMF6-based plasmid, designated pHEPtk1, is included in the following pages and was earlier disclosed in pending U.S. patent application Ser. No.07/162,885 and published [26]. Plasmid pHEPtk1 contains independently expressed P450IIA2 and microsomal epoxide hydrolase (EH) cDNAs, the gene for hygromycin resistance, and further contains sequences from the origins of replication of the Epstein-Barr virus (EBV) and pBR322 which allow it to replicate autonomously in both EBV-transformed lymphoblastoid cells and E. coli [24]. pHEPtk1 is 13.1 kb in size and possesses unique sites for the restriction enzyme Hind III, which may be used for the insertion of the DNA of interest.

The constructions of the pEBVHistk vector as well as its derivative plasmids, designated pH44 and pH441, are disclosed in the following pages. The construction of pEBVHistk was earlier disclosed in pending U.S. patent application Ser. No. 07/162,885 and has been reported [27]. The construction is reproduced in part herein to facilitate enablement. Plasmid pHBVHistk, contains the E. coli HisD gene which confers 1-histidinol resistance [27] and contains sequences from the origins of replication of the EBV and pBR322 which allow it to replicate autonomously in EBV-transformed lymphoblastoid cells and E. coli. Plasmid pEBVHistk is 9.6 kb in size and possesses unique sites for the restriction enzymes Sal I, Nhe I, and Bam HI, which may be used for the insertion of the DNA of interest. Under appropriate selection conditions, plasmid pHEPtk1 is maintained at 5 copies per diploid cell DNA and pEBVHistk, as well as its derivative plasmids, is maintained at 40 copies per diploid cell DNA.

Restriction endonucleases, the Klenow fragment of DNA polymerase I, and T4 DNA ligase were obtained from New England Biolabs, Beverly, Mass. and were used according to the manufacturer's recommendations. Calf intestine DNA, alkaline phosphatase and T4 polynucleotide kinase were purchased from Pharmacia, Piscataway, N.J. [$^{32}$p]-labeled ATP and deoxynucleotides were purchased from Dupont/NEN, Boston, Mass.

Isolation of the P450IIA2 clone.

Isolation of the P450IIA2 clone is described below and was earlier disclosed in pending U.S. application Ser. No. 07/162,885.

The strategy for the isolation of the P450IIA2 clones was as follows. A partial cDNA sequence of a human cytochrome P450IIA2, isolated by hybridization with the rat CDNA encoding P450e, was reported by Philips and colleagues [28]. The cDNA was of sufficient length to encode only two-thirds of the gene. We selected an oligonucleotide at the 5' end of the published sequence to use as a probe of the human liver cDNA library.

The human liver cDNA library HL1001b was plated according to standard procedures [29] at a density of $4.25 \times 10^4$ phage per 150 mm petri dish. Plaque replica lifts were performed on Schleicher & Schuell BA-85 nitrocellulose filters according to standard procedures [30]. The P450 oligomer (d[pACATT-GGAGAATGTGCGGAT]) was end-labeled with polynucleotide kinase and [gamma-$^{32}$p] ATP as described [30].

Hybridizations with the P450 oligomer were performed at 30° C. in 37.8% formamide, 5× Denhardt's solution [31], 5× SSPE (11), 0.1% sodium dodecyl sulfate (SDS) and 250 ug/ml denatured herring sperm DNA for 16 hours. Following hybridization, the plaque lifts were given three fifteen minute washes at room temperature and three fifteen minute washes at 42° C., each in 500 ml of 2× SSC [32] and 0.1% SDS. The washed filters were then affixed to a sheet of Whatman 3MM filter paper, covered with plastic wrap and exposed to Kodak XAR X-ray film for 1 to 24 hours. Film was developed according to the manufacturer's instructions. Positive plaques were picked using Pasteur pipettes and were purified to homogeneity by successive rounds of plaque replica lifts and screening with the oligonucleotide probe. Of the 125 positive clones, 31 were selected for DNA isolation and analysis. DNA was isolated from purified recombinant phage using the Lambdasorb ™ phage adsorbent protocol of Promega, Madison, Wis. Lambdasorb ™ is a preparation of rabbit polyclonal antibodies directed against bacteriophage lambda particles, in which the antibodies are covalently linked to formalin-fixed *Staphylococcus aureus* bacterial cells. Bacteriophage lysates, prepared according to standard procedures [30], were incubated with 0.01 volume of Lambdasorb ™ for 30 minutes at 0° C. The absorbed phage were precipitated by centrifugation at 7500 RPM in a Beckman Microfuge II for 10 minutes. The precipitated phage were resuspended in 1 ml phage suspension buffer (10 mM Tris-HCL, pH 7.5, 100 mM NaCl, 10 mM MgCl$_2$, 0.01% gelatin) and centrifuged at 13,000 RPM for 1.5 minutes. The supernatant was discarded. This was repeated, following which the pellet was resuspended in 0.5 ml 10 mM Tris-HCL pH 7.8, 10 mM EDTA and heated at 70° C. for 5 minutes to release the phage DNA from the Lambdasorb ™. The preparation was centrifuged at 13,000 RPM for 2 minutes to pellet the absorbent, following which the supernatant was extracted twice with a 1:1 mixture of Tris buffered phenol/chloroform [30] followed by a single extraction with chloroform. The supernatant was then supplemented with 0.25 ml 5M NaCl and 0.25 ml of 30% polyethylene glycol (of an approximate molecular weight of 8,000 daltons) in 1.5M NaCl, following which it was mixed well and incubated on ice for 30 minutes. The mixture was centrifuged at 13,000 RPM for 5 minutes, the supernatant was discarded and the DNA pellet was rinsed in 70% ethanol and re-centrifuged. The DNA pellet was dried under vacuum and resuspended in 25 microliters of 10 mM Tris-HCL pH 7.8, 0.1 mM EDTA. The isolated DNA was digested with Eco RI and subjected to electrophoresis on 0.8% agarose gels to determine the size of the cDNA inserts. The gels were stained with 0.5 ug/ml ethidium bromide and bands were visualized under ultraviolet illumination. The clones fell into seven classes based upon insert size of which three were sufficiently large to encode the entire P450IIA2 gene. The 1.8 kb Eco RI fragment of one large clone, designated 91D, was isolated from the agarose gel according to standard protocols [30]. (FIG. 1) To provide a convenient source of 91D DNA, the fragment was introduced into and propogated in pBR322. The 91D fragment was introduced into the Eco RI site of pBR322 [33], as follows: pBR322 DNA was digested with Eco RI and subsequently treated with calf intestinal alkaline phosphatase to prevent recircularization of the vector. The Eco RI cDNA fragment was combined with the Eco RI-cut pBR322 in three-fold molar excess and ligated into the vector using T4 DNA ligase. The ligated plasmid was then used to transform *E. coli* HB101, according to the rubidium chloride procedure described in Maniatis et al. [30]. Transformed colonies were selected on Luria broth plates supplemented with ampicillin (50 ug/ml). Several colonies were expanded to 5 ml liquid cultures and plasmid DNA was isolated according to the alkaline lysis miniprep procedure described in Maniatis et al. [30]. The DNA was digested with Eco RI and subjected to electrophoresis as above to verify the presence of the 1.8 kb band. One such colony was identified and expanded to a 1 liter liquid culture for isolation of milligram quantities of DNA of the recombinant plasmid, p91D. This was performed according to Garger et al. [34]. The plasmid DNA was then digested with a series of restriction endonucleases and a detailed restriction map was prepared. Fragment 91D was compared at corresponding regions with the fragment described by Phillips et al. [28]. Fragment 91D shares sites for the following restriction enzymes with the fragment described by Phillips et al: Bam HI, Hinc II, OxaN I, Rsa I, Sac I, SfaN I, Sph I, Stu I, Sty I and Xmn I. A conflict was observed in the position of the site for the restriction enzyme FnuD II, which could represent a sequence difference due to allelic variation. Based on the similarities in the restriction maps we have assigned the 91D isolate to the P450IIA2 class.

The location of the 5' end of 91D was determined by digestion with restriction enzyme Bam HI followed by agarose gel electrophoresis and Southern blotting [32]. The blots were probed with the 5' oligomer and the assignment of the location of the 5' end was based upon the pattern of hybridization.

Isolation of the Epoxide Hydrolase clone.

Isolation of the human epoxide hydrolase (EH) gene is disclosed below and was earlier disclosed in pending U.S. application Ser. No. 07/162,885.

The strategy for the isolation of the human epoxide hydrolase (EH) gene required two parts, as follows: The gene for the rat EH has been isolated [35] and sequenced [36] and could therefore be used as a probe of a human cDNA library in order to isolate the human gene. An oligonucleotide was prepared from the published sequence and was used to isolate a rat EH clone, designated 14A.

The rat liver cDNA library RL1001b was plated at a density of 4.3×10$^4$ phage per 150 mm plate and nitrocellulose replica lifts were performed. The oligomer (d[pCCCCAGTCCCCGCCTTGAAT]) was end-labeled with [gamma-=$^p$] ATP as above. Hybridizations with the rat epoxide hydrolase oligomer were performed at 30° C. in 50% formamide, 5× Denhardt's solution, 5× SSPE, 0.1% SDS and 250 ug/ml denatured herring sperm DNA. After hybridizing for 16 hours, the filters were subjected to three 15 minute washes at room temperature, two 15 minute washes at 42° C. and one 15 minute wash at 52° C., each in 2× SSC and 0.1% SDS. XAR X-ray film was exposed and developed as described above. Positive plaques were picked using Pasteur pipettes and were purified to homogeneity by successive rounds of screening. DNA was isolated from recombinant phage as above using the Lambdasorb ™ protocol of Promega, Madison, Wis., and was digested with Eco RI to determine the size of the cDNA inserts. The cDNAs fell into seven classes which ranged in size from 0.74 kb to 1.6 kb. A representative of the largest class (clone 14A, 1.6 kb) was selected for further analysis.

The identity of 14A was verified by extensive restriction mapping and comparison with a computer-generated map of the published rat EH sequence. The 1.6 kb Eco RI fragment of 14A was subcloned into the Eco RI site of pBR322, resulting in the plasmid p14A. A 5' Eco RI-Bam HI fragment of p14A was used to probe the human liver and placenta cDNA libraries, HL1001b and HL1008. HL1001b was plated at a density of $4.3 \times 10^4$ plaques per 150 mm plate and HL1008 was plated at a density of $5 \times 10^4$ plaques per plate. The 5' Eco RI-Bam HI fragment of p14A (0.46 kb) was nick translated to a specific activity of $5 \times 10^7$ cpm/ug with [alpha-$^{32}$P] dCTP and TTP [30], and the plaque lifts were probed with the fragment in 50% formaldehyde hybridization solution as above. The plaque lifts were given three 15 minute washes at room temperature followed by one 30 minute wash at 68° C., each in 2× SSC and 0.1% SDS. A total of 42 positive clones were identified, of which 36 were found in the liver library and six were found in the placenta library, DNA from 14 clones was isolated. Restriction analysis determined that the clones fell into eight classes based upon size. The largest clone, 167D, was of sufficient length (1.93 kb) to encode the entire EH gene. (FIG. 2) The presence of two internal Eco RI sites necessitated the use of alternate restriction enzymes in the subcloning of the sequence. Clone 167D was excised with Kpn I and Pvu I which resulted in the subcloning of 2.24 kb of phage DNA flanking the cDNA. The overhanging 3' ends were rendered blunt-ended with Klenow fragment of *E. coli* DNA polymerase I and Hind III linkers were kinased and ligated to the fragment [30]. The 4.17 kb fragment was inserted into the Hind III site of pBR322. Following transformation of HB101, isolation of DNA from transformed colonies and digestion with Hind III to ascertain the presence of the 4.17 kb 167D fragment, a plasmid designated p167D was selected. Plasmid DNA was isolated and a detailed restriction map was prepared. As was described above for clone 91D, the determination of the 5' end of clone 167D was achieved by Southern hybridization of an Eco RI restriction digest with the 5' Eco RI-Bam HI fragment of the rat EH clone 14A.

The P450IA2 clone.

The P450IA2 cDNA (in the ECO RI site of pUC9) was originally obtained from Drs. Frank Gonzalez and Harry Gelboin at the National Cancer Institute. cDNA was isolated from the recombinant plasmid by digestion with Eco RI and DraI, to yield a 1.6 kb fragment containing the entire coding sequence. The restriction enzyme-digested sticky ends were rendered blunt-ended with the Klenow fragment of *E. coli* DNA Polymerase I and XhoI linkers were ligated to the fragment [30]. The modified cDNA was introduced into the unique Sal I site of the expression vector pMF6. (FIG. 3) Following transformation of HB101, isolation of DNA from transformed colonies and analysis of structure by restriction mapping, the plasmid was designated pMF6/IA2. The DNA was isolated from the plasmid and was subjected to partial digestion with Nar I to isolate and purify the 2.6 kb fragment containing the P450IA2 cDNA, the promoter and polyadenylation signal of HSVtk.

The P450IIIA4 clone.

The isolation of the P450IIIA4 clone has been published [38]. This clone was originally obtained from Drs. Frank Gonzalez and Harry Gelboin at the National Cancer Institute. cDNA was isolated from the recombinant plasmid by digestion with Bsu 36 I and partial digestion with Eco RI, to yield a 1.6 kb fragment [38] containing the entire coding sequence. The restriction enzyme-digested fragment was rendered blunt-ended and modified by the addition of Xho I linkers and introduced into the unique Sal I site of the pMF6 expression vector [39]. This vector was designated pMF6/3A4. A 2.6 kb Nar I fragment containing the P450IIIA4 cDNA, the promoter and polyadenylation signal of HSVtk was isolated and purified.

Isolation of the P450IIE1 clone.

The human cytochrome P450IIE1 cDNA was isolated using an oligonucleotide probe whose sequence was based on the published sequence for human P450IIE1 cDNA [40]. The oligonucleotide was complementary to basepairs 82 to 101 in the coding sequence of the cDNA and had a sequence of 5'GCAGCTGGAATCTGCCCC 3'. The oligonucleotide was end labeled with $^{32}$p and used to screen a human liver cDNA library in λgt11 (HL1001b).

The human liver cDNA library HL1001b was plated according to standard procedures [29] at a density of $4.25 \times 10^4$ phage per 150 mm petri dish. Plaque replica lifts were performed on Schleicher & Schuell BA-85 nitrocellulose filters according to standard procedures [30]. The P450 oligomer (d[pACATT-GGAGAATGTGCGGAT]) was end-labeled with polynucleotide kinase and [gamma-$^{32}$P] ATP as described [30].

Hybridizations with the P450 oligomer were performed at 30° C. in 37.8% formamide, 5× Denhardt's solution [31], 5× SSPE [30], 0.1% sodium dodecyl sulfate (SDS) and 250 ug/ml denatured herring sperm DNA for 16 hours. Following hybridization, the plaque lifts were given three fifteen minute washes at room temperature and three fifteen minute washes at 42° C., each in 500 ml of 2× SSC [32] and 0.1% SDS. The washed filters were then affixed to a sheet of Whatman 3MM filter paper, covered with plastic wrap and exposed to Kodak XAR X-ray film for 1 to 24 hours. Film was developed according to the manufacturer's instructions. Positive plaques were picked using Pasteur pipettes and were purified to homogeneity by successive rounds of plaque replica lifts and screening with the oligonucleotide probe. Positive colonies were purified, the cDNA inserts were excised, Lambdasorb ™ subcloned into the Eco RI site pUC19 and restriction maps were generated. The restriction map of the largest isolate, designated 257A, showed considerable agreement with that of the published P450IIE1 cDNA [27].

In order to determine whether the cDNA isolate contained the complete coding sequence, 100 basepairs at the 5' end were directly sequenced in pUC19. Isolate 257A was found to be 11 basepairs short of the complete coding sequence. There were also 3 base substitutions in the isolate relative to that of Song et al [40], all of which were cryptic. A cDNA with the complete coding sequence was generated by blunt-end ligation of synthetic oligonucleotides. Isolate 257A was cut at the 5' cloning linker (Eco RI) and at the 3' end with Nde I. The DNA fragment was rendered blunt-ended with Mung Bean nuclease, and the synthetic oligonucleotides shown below were ligated onto the blunt-ended fragment.

```
         Xho I Start
5¹ TCGAG'AT GT CT GCCG 3¹
3¹     C TACAGACGGC 5¹
```

These oligonucleotides were synthesized to correspond to the published 5' cDNA coding sequence and to have Xho I "sticky ends" to facilitate subcloning into the expression vector pMF6 [27]. Ligation of the oligonucloetides onto the blunt-ended cDNA resulted in a sequence containing a single, conservative amino acid substitution at position 4 (alanine for leucine). This substitution is not expected to affect enzyme function. The ligated mixture was digested with Xho I and the desired fragment was purified and subcloned into the unique Sal I site in the expression vector pMF6. The correct construct was designated p257Atk2. A 2.6 kb NarI fragment containing the P450IIEI cDNA, promoter and polyadenylation signal for HVtk was isolated and purified according to standard procedures.

CONSTRUCTION OF pME23 AND pH441 EXPRESSION VECTORS

The following sections describe the construction of the pME23 and pH441 expression vectors which were used to transfect L3 cells. Plasmid pME23 contains P450IA2, P450IIA2 and mEH cDNAs. pME23 is derived from pHEPtk1, a pMF6-based plasmid containing the P450IIA2 and P450EH genes. Plasmid pH441 is derived from plasmid pH44, a pEBVHIStk-based plasmid, and contains two P450IIIA4 cDNAs and one P450IIE1 cDNA.

Figure 4:
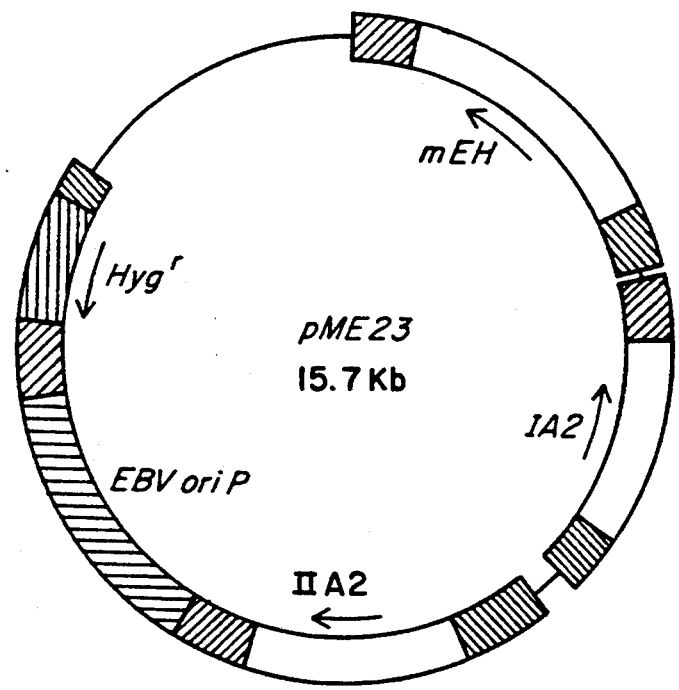
FIG. 4 is a restriction endonuclease map of the recombinant expression vector pME23 of the invention.
Figure 5:
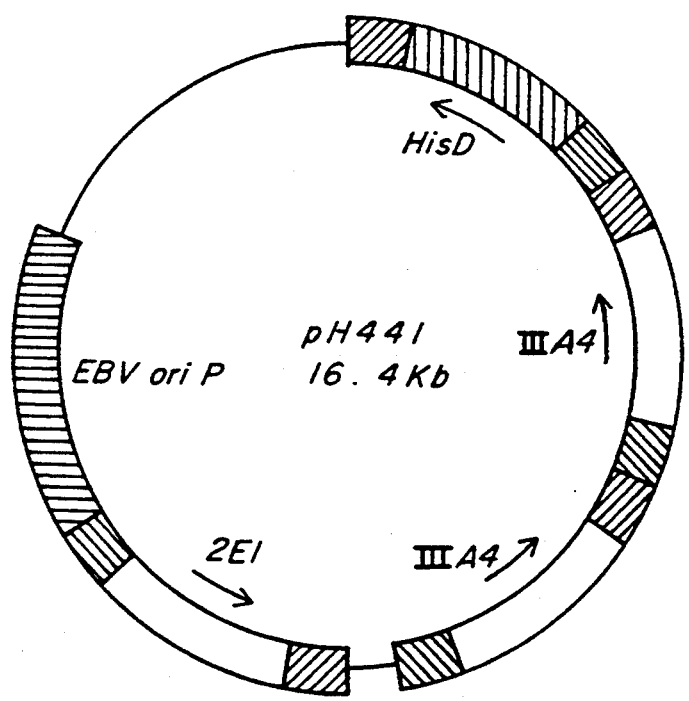
FIG. 5 is a restriction endonuclease map of the recombinant expression vector pH441 of the invention.

Schematic Maps of the pME23 and pH441 Vectors are shown in FIGS. 4 and 5, respectively. The thin line represents pBR322 sequences, the black box represents the Ori P sequences derived from EBV, the hatched boxes represent the hygromycin B resistance gene (FIG. 4) or the *E. Coli* His D gene (FIG. 5), the stippled boxes represent the HSV promoters, the cross hatched boxes represent the HSV polyadenylation signals and the open boxes represent the cDNAs. Identities of the cDNAs and direction of transcription are indicated on the figures.

A. Construction of Expression Vector pME23

A1. Construction of Expression Vector pHEPtk1.

Figure 6:
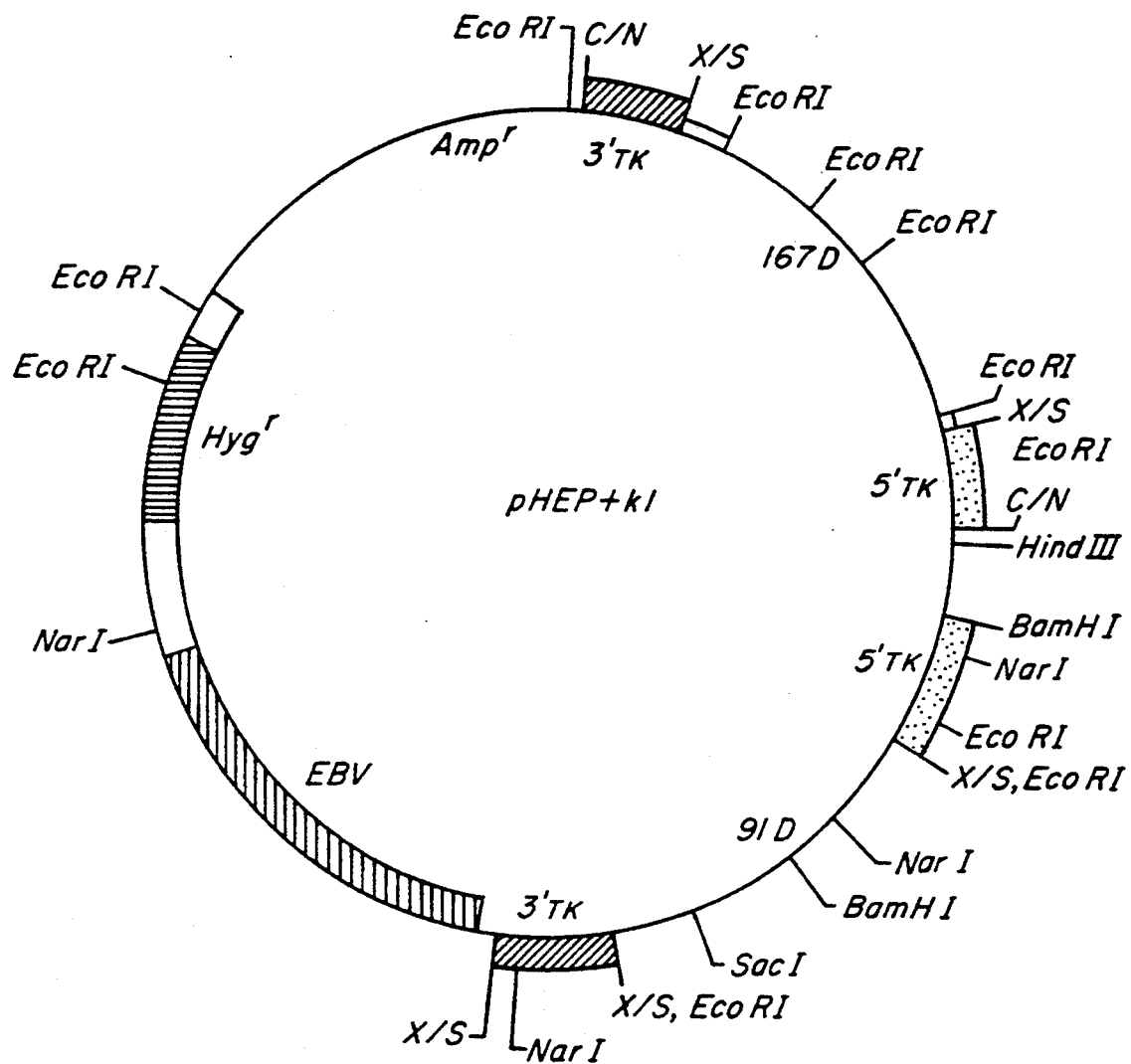
FIG. 6 is a restriction endonuclease map of the expression vector of FIG. 3 including the DNA fragments of both FIG. 1 and FIG. 2.

Construction of vector pHEPtk1 was disclosed in pending U.S. application Ser. No. 07/162,885 and is incorporated herein by reference. Plasmid pHEPtk1 (FIG. 6) contains transcriptional units for P450IIA2 and EH. The construction of this vector was as follows:

As determined by the restriction analyses, neither of the clones P450IIA2 nor EH was cut by Sal I or Xho I. Thus, constructing an expression vector having a promoter sequence and a poly A addition signal sequence separated by a unique Sal I site would allow easy insertion of the cloned fragments into the expression vector. The plasmid pHEBo has a unique Sal I site, and this plasmid was selected as the starting point for creating the expression vector with control regions separated by a unique Sal I site.

The expression vector for the P450IIA2 and EH genes was created as follows: Plasmid pHSV106 [36], bearing the Herpes simplex virus thymidine kinase gene, was digested with Pvu II, and then Xho I linkers were added [30]. The DNA was then digested with Sma I and Sal I linkers were attached to create fragments with Xho linkers at one end and Sal I linkers at the other end. Included was a 0.6 kb fragment bearing the 3' poly A addition signals of the HSV tk gene [41, 42], which could now be inserted into the Sal I site of pHEBo.

pHEBo was digested with Sal I and subsequently treated with calf intestinal alkaline phosphatase to prevent recircularization of pHEBo during the ligation step. The 0.6 kb fragments with Xho linkers at one end and Sal I linkers at the other were added and the DNA was ligated. Since both Xho linkers and Sal linkers will ligate to the Sal I cut in the pHEBo, two orientations of the fragment were possible. Of the two orientations, the fragment would be correctly inserted when the preserved Sal I site at the 5' end of the fragment was proximal to the Bam HI site of pHEBo, and the nonfunctional 3' Sal I-Xho I fusion site was distal to the Bam HI site. Following ligation, bacteria were transformed with the newly created plasmids and plasmid DNA was isolated from transformed colonies. Isolated plasmid DNA from different colonies was digested with Eco RI and with both Cla I and Sal I to determine the presence and orientation of the inserted HSV tk sequences. The plasmid having the correct orientation was designated p12L.

The 5' promoter sequences were isolated from pHSV106 by cutting the plasmid with Bgl II, filling in the ends with the Klenow fragment of *E. coli* DNA polymerase I [30] and adding Sal I linkers. The DNA was then cut with Bam HI to create a 0.7 kb fragment having a Bam HI cut site at the 5' end and a Sal I linker at the other 3' end. Then, plasmid p12L was cut with Bam HI and Sal I, the 0.7 kb fragment was added to the p12L cut DNA and the total DNA was ligated and used to transform HB101. DNA then was isolated from transformed HB101 colonies utilizing the miniprep procedure, and the DNA was digested with Pst I, Eco RI and both Bam HI and Sal I to identify the correct construction. The plasmid so obtained, designated pMF6, contained both 5' and 3' controlling sequences from the HSV tk gene and preserved the uniqueness of the Sal I site for use in the insertion of genes to be expressed in the human lymphoblasts.

A2. Introduction of the P450IIA2 cDNA into the Expression vector pMF6.

Figure 7:
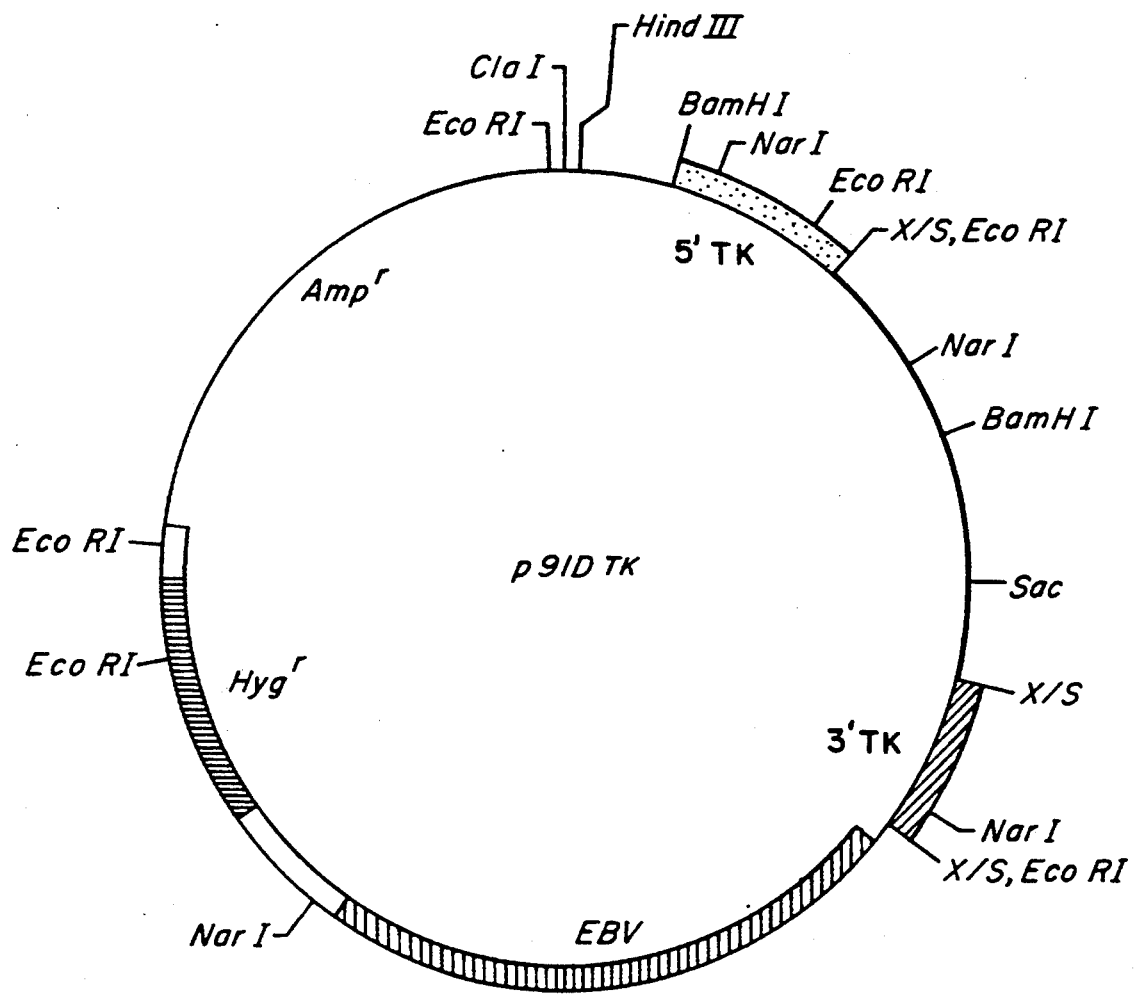
FIG. 7 is a restriction endonuclease map of the recombinant expression vector of FIG. 3 including the DNA fragment of FIG. 1.

Plasmid pMF6 DNA was digested with Sal I and treated with calf intestine phosphatase, as above. The P450IIA2 clone 91D was excised from plasmid p91D with Eco RI. The resulting fragment was made blunt-ended using the Klenow polymerase fragment and Xho I linkers were added, following which the fragment was ligated directly into the Sal I-cut pMF6. HB101 was transformed with the ligated plasmid, DNA was isolated from the resulting colonies and the orientation of the fragments relative to the HSV tk sequences was determined by digestion with Bam HI. The appropriate construction was designated p91Dtk. (FIG. 7)

A3. Introduction of the EH cDNA into the Expression Vector pMF6.

Figure 8:
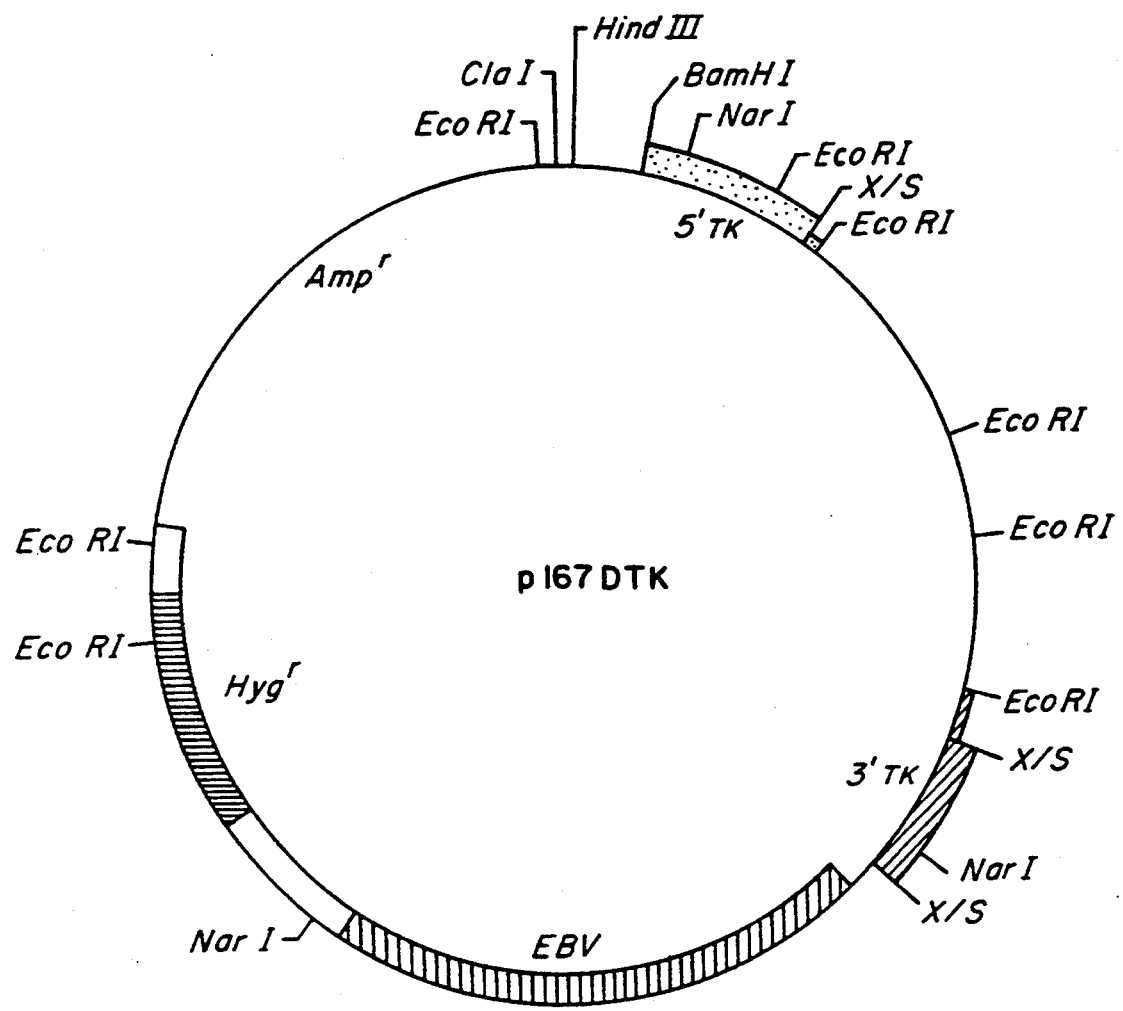
FIG. 8 is a restriction endonuclease map of the recombinant expression vector of FIG. 3 including the DNA fragment of FIG. 2.

The introduction of the EH clone into pMF6 was complicated by the presence of internal Eco RI sites in the clone. Extensive restriction mapping of plasmid p167D revealed that use of Nde I and Rsr II would allow excision of clone 167D with only 220 bp of flanking phage DNA (less than 50 bp at the 5' end and approximately 180 bp at the 3' end). The resulting fragment of 2.15 kb was rendered blunt-ended with Klenow and Xho I linkers were attached. The fragment was then ligated into Sal I-cut pMF6. DNA was isolated from transformed HB101 colonies and a recombinant plasmid bearing the EH clone in the appropriate orientation relative to the HSV tk sequences was identified by a double digestion with the restriction enzymes Hind III and Xba I. This plasmid was designated p167Dtk. (FIG. 8)

A4. Consolidation of P450IIA2 and EH cDNAs on a Single pMF6 Plasmid.

In order to simplify introduction of the novel activities into the improved lymphoblastoid cell line L3, plasmid pHEPtk1 carrying both of the newly isolated cDNAs (P450IIA2 and EH) together with their attendant control sequences was constructed. The entire expression region of p167Dtk, including the necessary HSV sequences at both the 5' and 3' ends, was excised with Nar I. The resulting 3.2 kb fragment was introduced into the unique Cla I site of p91Dtk. The 167Dtk sequences can be ligated into the p91Dtk plasmid in either of two possible orientations, both of which may be expected to be productive. Bacteria were transformed with the ligation mixture and DNA was isolated from transformed colonies using the alkaline lysis miniprep procedure. The orientation of the inserted DNA was determined by a double digestion with Hind III and Xba I, and plasmids with inserts in both orientations were obtained. In pHEPtk1, the 167Dtk sequences will be transcribed in the opposite direction from the 91Dtk sequences. In the alternate plasmid, designated pHEPtk2, the two genes are transcribed in the same direction.

A5. Introduction of the P450IA2 cDNA into Vector pHEPtk1 to Construct Expression Vector pME23.

Plasmid pHEPtk1 was digested with Hind III, the cut was rendered blunt ended and modified by the addition of Cla I linkers and then treated with phosphatase. The vector was ligated to the 2.6 kb Nar I fragment obtained from partial digestion of pMF6/IA2 [37] which contains the complete P450IA2 transcriptional unit described earlier.

HB101 was transformed with the ligated plasmid, DNA was isolated from the resulting colonies and the identity of the construct was verified by restriction mapping. The resulting construction was designated pME23. (FIG. 4)

B. Construction of Expression Vector pH441.

The following sections describe construction of the pEBVHIStk-based expression vector, pH441, having the cDNAs for P450IIIA4 and P450IIE1.

B1. Construction of Expression Vector pEBVHistk.

pEBVHistk was constructed as follows: the 2.5 kb Nar I fragment of pMF6 containing the EBV origin of DNA replication was introduced into Nat I digested pBR322 (Short HSV tk sequences at either end of this fragment not functional) and the construct was designated pEBV. Isolation of the 2.5 kb Nar I fragment was earlier disclosed in pending U.S. Application Ser. No. 07/162,885, a summary of which is reproduced below to facilitate enablement. The 2.5 kb Nar I fragment of pMF6 containing the E. coli HisD gene (Cut with Ava II at the 5' end and Hind III at the 3' end, approximately 600 bp at the 3' end were removed with Bal31 nuclease) was introduced into the Cla I site of pEBV to generate pEBVHis. Finally, the 1.0 kb Nar I fragment of pMF6 was modified by the addition of Hind III linkers and introduced into the Hind III site of pEBVHis to generate pEBVHistk.

B2. Introduction of the P450IIIA4 Gene into Vector pEBVHistk to Construct Expression Vector pH44.

Plasmid pH44 was constructed as follows: the 1.6 kb Eco RI/Bsu36 I fragment of the P450IIIA4 cDNA [38] containing the entire coding sequence was modified by the addition of Xho I linkers. The modified cDNA was introduced into the unique Sal I site of the pMF6 expression vector [39]. This vector, designated pMF6/3A4, was digested with Nar I and a 2.6 kb Nar I fragment containing the entire P450IIIA4 transcriptional unit (described above) was isolated and ligated into the pEBVHis vector [43] after modifying the Hind III site by the addition of Cla I linkers and treating with calf intestine phosphatase. This vector confers resistances to 1-histidinol and is maintained at high copy number (40 per cell). In order to partially compensate for the anticipated lower expression of P50IIIA4, a plasmid containing 2 complete P450IIIA4 transcriptional units was constructed and designated pH44. To facilitate this construction in a single step, a 10:1 molar ratio of P450IIIA4-containing 2.6 kb fragment to vector was used in the ligation.

B3. Introduction of the P450IIE1 cDNA into Vector pH44 to Construct Expression Vector pH441.

Plasmid pH44 was subjected to a Nar I partial digest and calf intestine phosphatase treatment. The vector was ligated to the 2.6 kb Nar I fragment of p257Atk2 [27] which contains a complete P450IIE1 transcriptional unit as described above. The identity of the construct was verified by restriction mapping and the resulting plasmid was designated pH441. (FIG. 5)

TRANSFECTION PROCEDURES

Two human lymphoblastoid cell lines were established by introducing the above-described plasmids into L3 cells using protoplast fusion. The first cell line, designated MCL-1, included pHEPtk1 containing P450IIA2 and microsomal epoxide hydrolase cDNAs. The second cell line, designated MCL-5, included plasmids pH441 and pME23. Construction of these cell lines is described below.

Construction of the MCL-1 Cell Line:

The plasmid pHEPtk1 was introduced into L3 cells using protoplast fusion [12]. E. coli HB 101 containing the plasmid pHEPtk1 were grown in Luria broth containing 50 ug/ml ampicillin (150 ml total volume). When the bacteria concentration yielded a OD$_{600}$ of 0.6, 200 ug/ml chloramphenicol was added to the culture and the culture was stirred overnight. Bacteria were centrifuged 2000×g for 10 minutes and the cell pellet resuspended in 1.5 ml of HBS-20 (20 mM HEPES, 20% sucrose, pH 7.1) and 0.48 ml of a 10 mg/ml lysozyme solution (in HBS-20, filter sterilized) was added. The bacteria were incubated at room temperature for 45 minutes. The lysozyme reaction was terminated by the addition of 0.24 ml of 1.25M CaCl$_2$. Excess Ca$^{++}$ was chelated by adding 0.6 ml of 0.25M EDTA. The above protoplast preparation was diluted by the addition of 6 ml of HBS-9 (20 mM HEPES, 9% sucrose, pH 7.1).

L3 cells (4×10$^7$ cells) were centrifuged and the cell pellet dispersed by tapping the tube. 1.5 ml of PEG-fusion reagent (PEG-fusion reagent consisted of 48% (w/v) polyethylene glycol purified according to [36] with the balance RPMI medium 1640) was added to the cells. 2.5 ml of the protoplast suspension was added immediately and the resulting suspension was centrifuged at 800×g for 3 minutes. The pellet was dispersed by tapping the tube, 1.5 ml PEG-fusion reagent was added and the cells were incubated for 1 minute. The PEG-fusion reagent was diluted with 50 ml of normal medium, the cells were centrifuged and resuspended in 80 ml of normal medium containing 100 U/ml penicillin, 100 ug/ml streptomycin and 100 ug/ml gentamycin. One day after protoplast fusion cells were diluted to 80 ml at $4 \times 10^5$ cells per ml and 300 ug/ml hygromycin B was added. Two days after protoplast fusion the cell dilution and hygromycin B addition was repeated. Four days and six days after protoplast fusion 40 ml of the culture was centrifuged, resuspended in 40 ml of fresh normal medium, added back to the culture and 300 ug/ml hygromycin B was added to the culture. Ten days after protoplast fusion the bulk population began to grow; cells were diluted to $2 \times 10^5$ cells per ml (80 ml total volume). Thereafter cells were either diluted to $2 \times 10^5$ cells per ml and 100 ug/ml hygromycin B was added every 2 days or cells were diluted to $1 \times 10^5$ cells per ml and 200 ug/ml hygromycin B added every 3 days. The cell line resulting from this procedure was designated MCL-1.

Construction of the MCL-5 Cell Line:

A. Transfer of Plasmid pH441 into L3 cells.

Plasmids pH441 and pME23 were introduced sequentially into the L3 cell line via protoplast fusion. Plasmid pH441 was introduced first.

Plasmid pH441 was introduced into L3 cells using protoplast fusion [31]. *E. coli* HB 101 containing the plasmid pH441 were grown in Luria broth containing 50 ug/ml ampicillin (150 ml total volume). When the bacteria concentration yielded a $OD_{600}$ of 0.6, 200 ug/ml chloramphenicol was added to the culture and the culture was stirred overnight. Bacteria were centrifuged $2000 \times g$ for 10 minutes and the cell pellet resuspended in 1.5 ml of HBS-20 (20 mM HEPES, 20% sucrose, pH 7.1) and 0.48 ml of a 10 mg/ml lysozyme solution (in HBS-20, filter sterilized) was added. The bacteria were incubated at room temperature for 45 minutes. The lysozyme reaction was terminated by the addition of 0.24 ml of 1.25M $CaCl_2$. Excess $Ca^{++}$ was chelated by adding 0.6 ml of 0.25M EDTA. The above protoplast preparation was diluted by the addition of 6 ml of HBS-9 (20 mM HEPES, 9% sucrose, pH 7.1).

L3 cells (2 to $3 \times 10^7$ cells) were centrifuged and the cell pellet dispersed by tapping the tube. 1.5 ml of PEG-fusion reagent (PEG-fusion reagent consisted of 48% (w/w) polyethylene glycol 1450 purified according to [55] with the balance RPMI medium 1640) was added to the cells. Unless otherwise specified, a reference to normal medium in this protocol indicates RPMI medium 1640, supplemented with 9% Horse serum. 2.5 ml of the protoplast suspension was added immediately and the resulting suspension was centrifuged at $800 \times g$ for 3 minutes. The pellet was dispersed by tapping the tube, 1.5 ml PEG-fusion reagent was added and the cells were incubated for 1 minute. The PEG-fusion reagent was diluted with 50 ml of normal medium, the cells were centrifuged and resuspended in 80 ml of normal medium containing 100 U/ml penicillin, 100 ug/ml streptomycin and 100 ug/ml gentamycin (PSG). One day after protoplast fusion, $2.6 \times 10^7$ cells were centrifuged ($1000 \times g$ for 5 min.) and resuspended in medium containing 0.5 mM 1-Histidinol (without 1-histidine) and PSG as described above. Five days after protoplast fusion the culture was diluted 50 ml to 80ml with the same medium. Eight days after protoplast fusion 50 ml of the culture was centrifuged, resuspended in 20 ml of the same medium and added back to the culture. Eleven days after protoplast fusion the culture was diluted by the addition of 30 ml medium containing 2 mM Histidinol. From this point forward the cell concentration was determined every 2 to 5 days and when it exceeded $2.5 \times 10^5$ cells/ml the culture was diluted (without 1-Histidine) and PSG. Twenty three days after protoplast fusion the culture was diluted 58 to 100 ml by the addition medium containing 2 mM 1-Histidinol (without 1-histidine) and PSG. Twenty nine days after protoplast fusion the culture was diluted to $1.5 \times 10^5$ cells/ml in 100 ml with the same medium. Thirty three and thirty seven days after protoplast fusion the culture was again diluted as described above. Forty and forty two days after protoplast fusion, the culture was diluted to $2 \times 10^5$ cell/ml in 100 ml with the same media. Forty four days after protoplast fusion, the culture was diluted to $1 \times 10^5$ cells/ml in 100 ml with the same media. Forty seven days after protoplast fusion, the cells were plated in 96 well microtiter plates in the above media. Cells were aliquotted over 8 plates at an average of 0.5 cells per well. The plates were incubated for 12 days. Colonies were isolated and scaled-up in media-containing 2 mM 1-histidinol (without 1-histidine) to bulk cultures (approximately 100ml).

P450IIIA4 (as measured as testosterone 6($\beta$) hydroxylase activity), P450IIE1 (as measured as sensitivity to the cytotoxicity of N-nitrosodimethylamine), and native P450IA1 (as measured as 7-ethoxy-resorufin deethylase activity) enzymatic activities and the structure and copy number (via southern Blotting of Eco RI digested genomic DNA) of the vector were verified in the clonal populations. One clonal population was chosen for subsequent transfection. This cell line containing approximately 40 copies of the pH441 vector, exhibited a testosterone 6-($\beta$) hydroxylase activity of 1.5–1.9 pmole product/$10^6$ cells min. Exposure to 100 ng/ml N-nitrosodimethylamine reduced survival to 0.18 relative to control (untreated) cells and exhibited 7-ethoxyresorufin deethylase activity (after pretreatment for 20 hrs with 0.1 uM dibenz(a,h)-anthracene) of 1.6 pmole product/$10^6$ cells-min.

It should be understood that the above protocol for protoplast fusion represents an actual embodiment of the invention and that the exact number of days between cell dilution may vary as a function of cell growth rates. Cell dilution is indicated when cells have doubled in number in comparison to the previous dilution. Accordingly, cell dilution is indicated when the cell count has exceeded between approximately $4 \times 10^5$ and $6 \times 10^5$ cells per ml.

Transfer of Plasmid pME23 into L3 cells previously transfected with Plasmid pH441.

The same protoplast fusion procedure described above in connection with the transfer of plasmid pH441 into an L3 cell line was employed for the insertion of plasmid pME23 into the pH441-transfected L3 cell line with the following exceptions:

Selection was based on resistance to both 2 mM 1-histidinol and hygromycin B. Following transfection, cells were cultured in media containing 2 mM 1-Histidinol (without 1-histidine), 30 ug/ml 4-aminolevulinic acid, 100 ug/ml penicillin, 100 ug/ml streptomycin and 100 ug/ml gentamycin. One day after protoplast fusion cells were diluted to 50 ml at $2.5 \times 10^5$ cells per ml and 400 ug/ml hygromycin B was added. Five days after protoplast fusion the cells were diluted 50 ml to 80 ml and 300 ug/ml Hygromycin B was added. Eight days after protoplast fusion 50 ml of the culture was centrifuged, resuspended in 20 ml of fresh medium, added back to the culture and 200 ug/ml hygromycin B was added to the culture. Eleven days after protoplast fusion the bulk population began to grow; cells were diluted to $2 \times 10^5$ cells per ml (80 ml total volume). Thereafter cells were either diluted to $2 \times 10^5$ cells per ml and 100 ug/ml hygromycin B was added every 2 days or cells were diluted to $1 \times 10^5$ cells per ml and 200 ug/ml hygromycin B added every 3 days. The bulk transfected population was designated MCL-5.

ASSAYS.

A. Enzyme Assays.

Enzyme activities were measured in whole cells. Coumarin 7-hydroxylase was measured according to the method of Greenlee and Poland [44] by adding 100 uM coumarin directly to the cell cultures and measuring fluorescence production after a two hour incubation. Microsomal epoxide hydrolase was measured according to the procedure of Glatt et al. [45] using $5 \times 10^6$ cells in a 0.5 ml total volume and incubating for 30 minutes. 7-ethoxyresorufin deethylase activity [46] was measured in whole cells according to [47]. All other enzyme assays utilized $1 \times 10^7$ cells in a 1 ml incubation volume. Acetanilide 4-hydroxylase was measured according to [48]. Chlorzoxazone 6-hydroxylase was measured according to [49]. Testosterone hydroxylase was measured according to Waxman et al [50].

B. Cytotoxicity and Mutagenicity Assays

Cytotoxicity was estimated by measuring growth after exposure to the procarcinogen. After cultures have resumed exponential growth, the cumulative growth of the mutagen-treated cultures was divided by the cumulative growth of the negative control cultures to yield relative survival.

(1) MCL-1 Cell line Experiments:

Stock cultures of MCL-1 cells were propagated in RPM1 1640 medium supplemented with 10% horse serum and 100-200 ug/ml hygromycin B as described above. Before use in a mutagenesis assay aliquots of stock MCL-1 cells were grown for three days in HAT medium (normal medium containing 100 uM hypoxanthine, 0.8 uM aminopterin, 35 uM thymidine and 100 ug/ml hygromycin B), centrifuged, resuspended in TH medium (HAT without aminopterin) and grown for three days with dilutions by normal medium containing hygromycin B (100 ug/ml). The HAT/TH treatment removes pre-existing tk and hgprt mutants.

Aliquots of MCL-1 cells ($3 \times 10^7$) cells in 60 ml) were exposed to one or more concentrations of the test chemical, to solvent alone and to a known mutagen, usually in replicate cultures, for 28 hr. Mutagen exposure was performed on normal medium containing 50 ug/ml hygromycin B. Chemical exposure was terminated by centrifuging the cultures and resuspending the cells in fresh medium (usually $3 \times 10^7$ cells in 80 ml) without hygromycin. Cultures were then passaged (generally every other day to $3 \times 10^7$ cells in 150 ml) to allow phenotypic expression of induced mutation (at least three days for the tk locus and at least seven days for the hgprt locus). After sufficient time to allow phenotypic expression of induced mutation, aliquots of the cultures were plated in 96 well microtiter plates to determine the mutant fraction. Cells were plated at an average of $2.5 \times 10^4$ per well in the presence of 4 ug/ml trifluorothymidine (usually three plates) to measure mutation at the tk locus, at an average of $2.5 \times 10^4$ (usually three plates) in the presence of 0.6 ug/ml 6-thioguanine to measure mutation at the hgprt locus and at an average of 2.5 cells per well (usually two plates) without selection to measure the plating efficiency. The plates were incubated for 12 or 13 days and scored for the presence or absence of a colony in each well. The calculation of mutant fraction and the statistical analysis were as described previously [51].

(2) MCL-5 Cell line Experiments:

Stock cultures of MCL-5 cells were propagated in RPM1 1640 medium (without histidine) supplemented with 9% horse serum, 100-200 ug/ml hygromycin B and 2 mM 1-histidinol and 30 ug/ml 4-aminolevulinic acid as described above. Before use in a mutagenesis assay aliquots of stock MCL-5 cells were grown for three days in HAT medium (stock culture medium containing 100 uM hypoxanthine, 0.8 uM aminopterin, 35 uM thymidine), centrifuged, resuspended in TH medium (HAT without aminopterin) and grown for three days with dilutions by stock culture medium. The HAT/TH treatment removes pre-existing tk and hgprt mutants.

Aliquots of MCL-5 cells ($3 \times 10^7$) cells in 60 ml) were exposed to one or more concentrations of the test chemical, to solvent alone and to a known mutagen, usually in replicate cultures, for 28 hr. Mutagen exposure was performed on normal medium containing 50-100 ug/ml hygromycin B, and 1-2 mM 1-histidinol and 15 to 30 ug/ml 4-aminolevulinic acid. Chemical exposure was terminated by centrifuging the cultures and resuspending the cells in fresh medium (usually $3 \times 10^7$ cells in 80 ml) without hygromycin or 1-histidinol. Cultures were then passaged (generally every other day to $3 \times 10^7$ cells in 150 ml) to allow phenotypic expression of induced mutation (at least three days for the tk locus and at least seven days for the hgprt locus). After sufficient time to allow phenotypic expression of induced mutation, aliquots of the cultures were plated in 96 well microtiter plates to determine the mutant fraction. Cells were plated at an average of $2.5 \times 10^4$ cells per well in the presence of 4 ug/ml trifluorothymidine (usually three plates) to measure mutation at the tk locus, at an average of $2.5 \times 10^4$ cells per well (usually three plates) in the presence of 0.6 ug/ml 6-thioguanine to measure mutation at the hgprt locus and at an average of 2.5 cells per well (usually two plates) without selection to measure the plating efficiency. The plates were incubated for 13 days and scored for the presence or absence of a colony in each well. The calculation of mutant fraction and the statistical analysis were as described previously [51].

EXAMPLES

Example 1

Enzyme Expression in MCL-5 Cells and Comparison to Expression with a Single cDNA per Vector.

Given the multiplicity of related vectors and the large number of Herpes Simplex virus (HSV) tk gene-derived promoters and polyadenylation signals (4 per vector), the stability of the cell line and the efficiency of expression of each cDNA were concerns.

To verify cDNA and native P450IA1 expression and also to examine stability of the cell line, a series of cytochrome P450 form-specific enzyme assays and procarcingen activations were measured as a function of time in cell culture (FIG. 9). The levels of the activities in MCL-5 cells were compared to those observed in cells transfected with a single cDNA with the same means of selection.

The levels of induced 7-ethoxyresorufin deethylase activity in MCL-5 cells were comparable to those observed in the untransfected L3 cell line [26]. Acetanilide 4-hydroxylase activity (P450IA2 specific), testosterone 6(beta)-hydroxylase (P450IIIA4-specific) and microsomal epoxide hydrolase activity in MCL-5 cells were comparable (within a factor of 2) to those observed in cells transfected with pMF6/IA2 [37], p91Dtk (pMF6/2A3; [52]), pH44 (pEBVHistk with two CYP-3A4 cDNAs;) and p167Dtk (pMF6/mEH; [26]) respectively. The levels of chlorzoxazone 6-hydroxylase (P450IIE1-specific) in MCL-5 cells were about 3 fold higher than in cells bearing pEBVHis/2E1. Based on these assays and comparisons, all cDNAs as well as the native P450IA1 were adequately expressed. It appears that there was no substantial promoter interference in these vector constructs.

It should be noted that although higher levels of stable expression for each of the above cDNAs have been achieved in constructs containing a single cDNA, this invention achieves expression of a multiplicity of P450 forms. There is certainly an upper limit to the P450 content (presently unknown) which will be stably supported in this cell line. These constructions were designed such that the total P450 content would be no more than that previously observed to be stably supported in this system (e.g. cells bearing P450IIA2 in the pEBVHistk vector contain about 1 pmole P450 per million cells).

This was achieved by placing two inefficiently expressed P450 cDNAs (P450IIIA4 and P4502E1) in the high copy number vector (pEBVHistk) and two efficiently expressed P450 cDNAs in the low copy number vector (pMF6). Thus the total anticipated P450 content was kept below 1 pmole/million cells.

The stability of expression at the enzyme level was determined by monitoring the levels of the enzyme activities as a function of time of growth in cell culture. For this experiment we initially cultured the transfected cells and scaled-up the size of the culture sufficiently to establish a freezer stock of several hundred vials. The zero time point represented establishing a culture from this stock. Independent vials were thawed at different times points and were assayed simultaneously in cultures that were propagated for 6, 37 and 63 days (FIG. 9).

The levels of enzyme activities did not vary substantially as a function of time in culture. The maximum difference among two time points was less than a factor of 1.5. Analysis over a two month time frame indicates that the MCL-5 cell line is sufficiently stable to permit many applications including long-term, low-dose exposure experiments [53, 54] and transfer of the cell line to independent laboratories.

Based on P450-specific enzyme assays, we conclude that MCL-5 cells simultaneously express the human P450 forms which have been established to be primarily responsible for the activation of many procarcinogens. Therefore MCL-5 cells have the potential for being an effective screening tool for human procarcinogen activation.

Example 2

Procarcinogen Activation by MCL-5 Cells: Cytotoxicity and Mutagenicity Assay Procedures.

The following procedure is directed to cytotoxicity and mutagenicity assays following exposure of the MCL-5 cells to the procarcinogen benzo(a)pyrene. The identical procedure was used to assess cytotoxicity and mutagenicity for each of the procarcinogens tested.

Mutant fractions were determined at the hgprt locus for all procarcinogen concentrations and were also determined at the tk locus for the highest procarcinogen concentration. The results are presented in the following examples. In general, the negative control mutant fractions at the hgprt and tk loci in MCL-5 cells were comparable to those observed in the parent L3 cell line. This indicated that the expression of the cytochrome P450s was not substantially affecting the spontaneous mutation rate (possibly through the generation of activated oxygen species). This observation is consistent with our previous observations that P450 expression does not affect background mutant frequency [5–8].

In general, there was good agreement between hgprt and tk in the magnitude of the mutagenic response observed. Values were all within a factor of 2. This indicates that the tk locus can be used for many screening applications with a significant savings in time and materials because of the shorter phenotypic expression time at tk relative to hgprt.

Cytotoxicity was estimated by measuring growth after treatment. After cultures have resumed exponential growth, the cumulative growth of the mutagen-treated cultures was divided by the cumulative growth of the negative control cultures to yield relative survival. Induction of mutation at the hgprt and tk loci was measured by previously published protocols [51] with minor modifications. Human lymphoblasts were exposed to the mutagen for 28 hours. Each replicate culture contained $3 \times 10^7$ cells. After a 7 day phenotypic expression period, the mutant fraction was measured according to the procedures described above. Aflatoxin $B_1$, Benzo(a)pyrene, 3-Methylchloranthrene, 2-Acetoaminofluorene and Benzidine were dissolved in dimethylsulfoxide; N-Nitrosodimethylamine and N-Nitrosodiethylamine were dissolved in water for delivery to the cell cultures.

Example 3

MCL-5 Cell Line—Toxicity and Mutagenicity of Benzo(a)pyrene

The toxicity and mutagenicity of the carcinogen benzo(a)pyrene was determined using the procedure described above. Benzo(a)-pyrene is known to be metabolized by the P450IA1 to mutagenic species. This mutagenicity can be further potentiated by the action of epoxide hydrolase in concert with the P450IA1 to generate a vicinal diol-epoxide.

Figure 10:
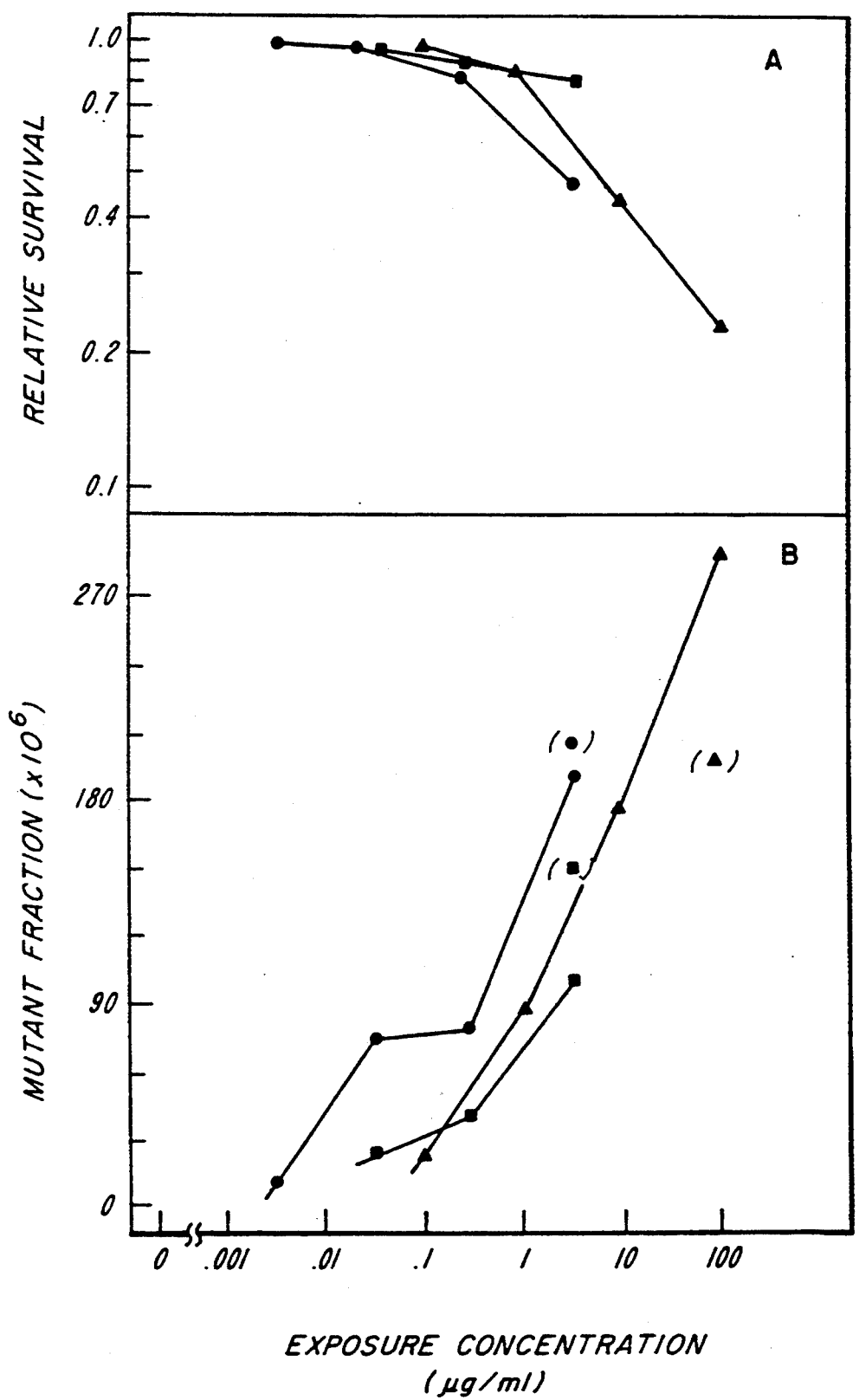
FIG. 10 is graph showing the relative survival (FIG. 10A) and sensitivity (FIG. 10B) of the MCL-5 cell line to the mutagenic effects of benzo(a)pyrene, 3-methylcholanthrene and N-nitrosodiethylamine.

The mutagenicity of benzo(a)pyrene; 3-methycholanthrene and N-nitrosodiethylamine was determined at the hgprt and tk loci in MCL-5 cells. Procarcinogen cytotoxicity and mutagenicity is illustrated in FIG. 10. Cells were exposed to the indicated concentrations of the mutagens for 28 hours. Each chemical was tested in at least two independent experiments with at least duplicate cultures in each experiment. Mean values are plotted. All concentrations were assayed for mutant fraction at the hgprt locus, the highest concentration was also assayed for mutant fraction at the tk locus. The tk locus data points are enclosed in parentheses. Procarcinogens are as follows: circles, benzo(a)pyrene; squares, 3-methycholanthrene and triangles, N-nitrosodiethylamine. The mean negative control mutant fractions were $2.8 \times 10^{-6}$ and $3.6 \times 10^{-6}$ at the hgprt and tk loci respectively.

Benzo(a)pyrene induced a significant mutagenic response at an exposure concentration of 3 ng/ml and monotonic increase in mutant fraction was observed over a 1000 fold concentration range (FIG. 10). Benzo(a)pyrene was not particularly cytotoxicity substantial increases in mutant fraction were observed in the absence of significant cytotoxicity and exposure to 3 ug/ml only reduced relative survival to 60%.

MCL-5 cells were 3 to 10 fold more sensitive to Benzo(a)pyrene than MCL-1 cells which express P450IIA3 and mEH under hygromycin B selection 26]. This observation is consistent with P450IA1 and mEH being primarily involved in this activation and suggests a potential role for other P450's in the activation of benzo(a)pyrene. Shimada, et al. [55] have reported that P450IIIA4 can activate Benzo(a)pyrene-7,8-diol in human liver microsomes.

Example 4

MCL-5 Cell Line—Toxicity and Mutagenicity of N-nitrosodiethylamine

N-nitrosodiethylamine cytotoxicity and mutagenicity were determined in MCL-5 cells (FIG. 10).

N-Nitrosodiethylamine induced a significant mutagenic response at an exposure concentration of 100 ng/ml, and like Benzo(a)pyrene, a monotonic increase in mutant fraction was observed over a 1000 fold concentration range including non-cytotoxic exposure concentrations (FIG. 10). We have previously demonstrated that both P450IIA2 and P450IIE1 can activate N-Nitrosodiethylamine [52]. The mutant fractions observed in MCL-5 cells was about 2 fold higher than predicted based on the sum of the mutant fractions in IIA2/Hyg cells and IIE1/Hol cells [52]. The higher mutant fractions in MCL-5 cells may be due to the apparently higher levels of P4502E1 as measured by chlorzoxazone 6-hydroxylase activity and N-Nitrosodimethylamine sensitivity.

Example 5

MCL-5 Cell Line—Toxicity and Mutagenicity of N-nitrosodimethylamine

Figure 11:
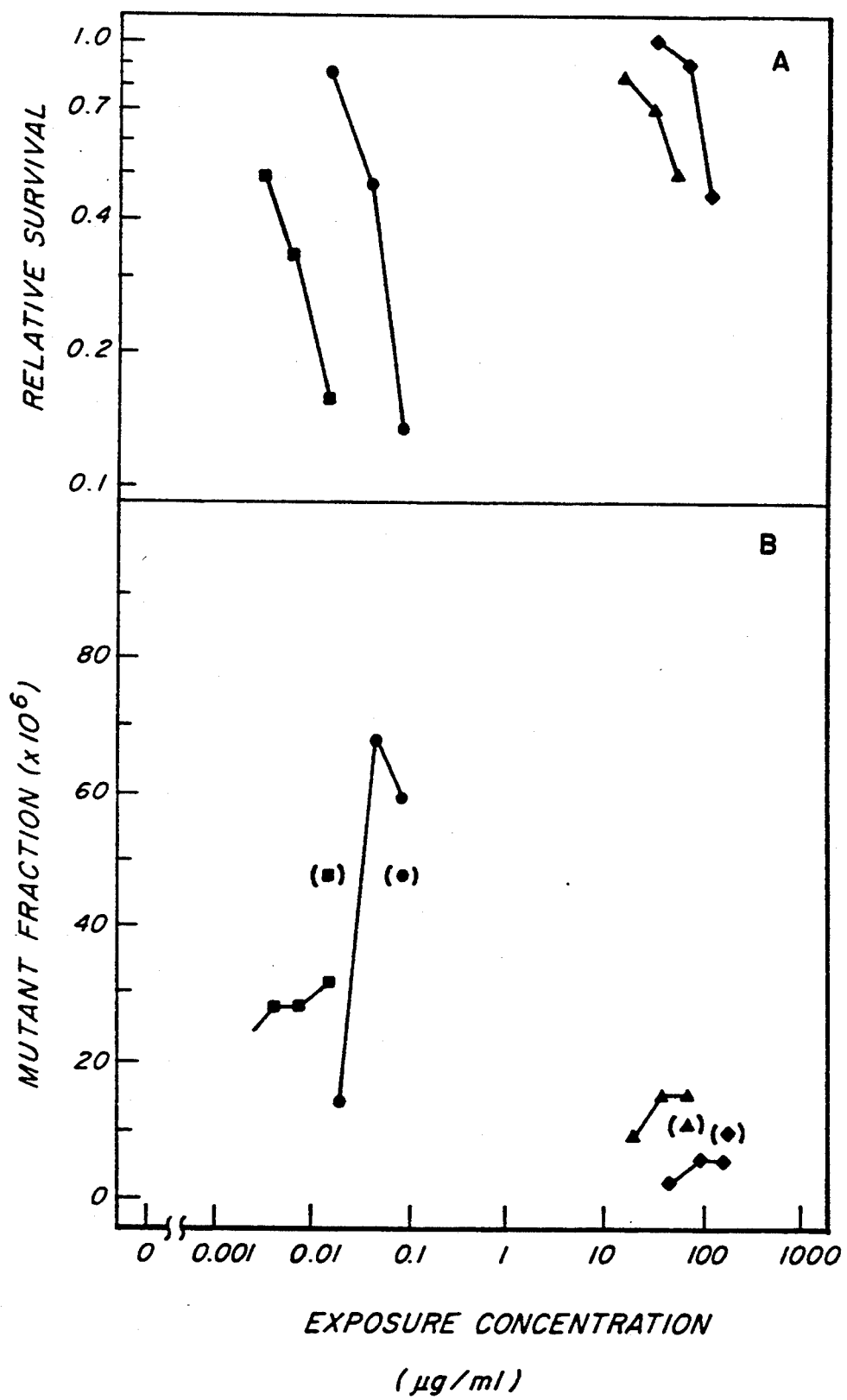
FIG. 11 is a graph showing the relative survival (FIG. 11A) and sensitivity (FIG. 11B) of the MCL-5 cell line to the mutagenic effects of aflatoxin $B_1$; N-nitrosodimethylamine, 2-acetoaminofluorene and benzidine.

N-nitrosodimethylamine cytotoxicity and mutagenicity were determined in MCL-5 cells (FIG. 11). Procarcinogens are indicated in FIG. 11 as follows: circles, N-nitrosodimethylamine; squares, Aflatoxin $B_1$ and triangles, 2-acetoaminofluorene and diamonds, benzidine. The experiments were performed and results plotted as described above.

N-Nitrosodimethylamine induced a significant increase in mutant fraction at an exposure concentration of 20 ng/ml (FIG. 11). This chemical was also quite cytotoxic. MCL-5 cells were about 3 fold more sensitive to N-nitrosodimethylamine than 2E1/Hol cells [52] which is consistent with the higher levels of chlorzoxazone 6-hydroxylase activity in MCL-5 cells. P450IIA2 plays a minor role in the activation of N-Nitrosodimethylamine (1000 fold less active than P450IIE1) which probably did not significantly contribute to the increased mutagenic response.

Example 6

MCL-5 Cell Line—Toxicity and Mutagenicity of Aflatoxin-B1 at the tk and hgprt Loci The toxicity and mutagenicity of the carcinogen aflatoxin $B_1$ was examined using the procedures described above. Aflatoxin-$B_1$ is metabolized by several cytochrome P450 enzymes including the P450IA1, P450IIA2, P450IIIA4 and P450IA2. Therefore it was anticipated that MCL-5 cells would be more sensitive to Aflatoxin $B_1$ induced mutagenicity.

Aflatoxin $B_1$ induced a significant increase in mutant fraction at an exposure concentration of 5 ng/ml (FIG. 11). Unlike Benzo(a)pyrene, 3-Methylchloranthrene and N-Nitrosodiethylamine, Aflatoxin $B_1$ was quite cytotoxic at low concentrations. We have previously observed Aflatoxin $B_1$ to be activated to a mutagen in IA2/Hyg, IIIA4/Hol and IIA2/Hyg cells (unpublished results) with IA2/Hyg cells being about 8 fold more sensitive than IIIA4/Hol cells which were about 15 fold more sensitive than IIA2/Hyg cells. The native cell line is also sensitive to Aflatoxin $B_1$. The sensitivity of MCL-5 cells was consistent with the sum of individual enzymatic activation capacities.

Example 7

MCL-5 Cell Line—Toxicity and Mutagenicity of 3-Methylchloranthrene

3-Methylchloranthrene induced a significant increase in mutant fraction at an exposure-concentration of 30 ng/ml and a monotonic increase in mutant fraction was observed over a 100 fold concentration range (FIG. 10). Again, substantial increases in mutant fraction were observed in the absence of significant cytotoxicity.

The mutant fractions observed in MCL-5 cells for Benzo(a)pyrene, N-nitrosodiethylamine and 3-Methylchloranthrene were among the highest observed in this system and were greater than many direct-acting alkylating agents. This observation underscores the substantial procarcinogen activating capacity in MCL-5 cells.

Example 8

MCL-5 Cell Line—Toxicity and Mutagenicity of 2-Acetoaminofluorene

2-Acetoaminofluorene has been reported to be activated by P450IA1 and P450IA2 [56]. 2-Acetoaminofluorene induced a significant increase in mutant fraction at an exposure concentration of 10 ug/ml as illustrated in FIG. 11. The response in MCL-5 cells was greater than that observed in the parent AHH-1 cell line and thus was consistent with one of the transfected and higher native P450IA1 activities mediating the activation. Further testing with cell lines expressing single cDNAs will be required to establish which form(s) were responsible.

Example 9

MCL-5 Cell Line—Toxicity and Mutagenicity of Benzidine

Benzidine induced a very modest increase in mutant fraction (2 to 3 fold, FIG. 11). The response in MCL-5 cells was similar to that observed in parent AHH-1 cell line (discussed further below). Indicating that metabolism by the transfected activities was probably not the rate limiting step for the activation of this compound to a mutagen.

Example 10

Comparison of MCL-5 Cell Line Sensitivity To Parent AHH-1 Cell Line

In order to further illustrate the effects of cDNA transfection, the sensitivity of the MCL-5 cell line was compared to that of the parent AHH-1 cell line which contains only native P450IA1 activity. For this comparison, the concentrations of mutagens necessary to yield a doubling in mutant fraction at the hgprt locus were calculated by linear interpolation. A doubling in mutant fraction represents a significant increase in mutant fraction. This comparison was possible for all chemicals except 3-Methylchloranthrene for which data was not available on the AHH-1 cell line. Both AHH-1 and MCL-5 cells have comparable negative control mutant fractions at the hgprt locus (2.5 to $3 \times 10^{-6}$). This comparison is presented in FIG. 12. For all procarcinogens except Benzidine the MCL-5 cell line was significantly more sensitive that AHH-1 cells. The nitrosamines were more than 10,000 fold more active, Benzo(a)pyrene and Aflatoxin $B_1$ were about 1000 fold more active and 2-Acetoaminofluorene was 3 fold more active in MCL-5 cells. Only Benzidine gave comparable responses in both cell lines. Based on the mutagenic responses observed in MCL-5 cells and the comparisons to AHH-1 cells, the procarcinogen activating capacity has been substantially improved by the transfection procedure. MCL-5 cells were very sensitive to the mutagenic effects of two polycyclic aromatic hydrocarbons, two nitrosamines, a mycotoxin and an aromatic amide. These results indicate that this cell line can activate a spectrum of procarcinogens.

Example 11

Procarcinogen Activation by MCL-1 Cells: Cytotoxicity and Mutagenicity Assay Procedures.

(a) MCL-1 Cell Line: Metabolism of benzo(a)pyrene

The MCL-1 cell line's capacity to metabolize benzo(a)pyrene was studied to verify that the cell line's metabolic capacity had been altered desirably. For the purposes of comparison, the metabolism of benzo(a)pyrene was also studied in AHH-1 tk± cells (unaltered metabolic capacity) and L3 cells (higher native metabolic activity).

Human lymphoblastoid cells ($3 \times 10^5$ cells per ml) were incubated in the presence of $^3$H-benzo(a)pyrene (2 Ci/mmol) (Dupont/NEN, Boston, Mass.) for 16 hours. The metabolites were extracted with ethylacetate and the ethylacetate extract was then dried with anhydrous magnesium sulfate. The metabolites then were isolated as a solid from the extract by evaporating the extract under a stream of nitrogen. The metabolites were then redissolved in 100 ul methanol and separated using a high performance liquid chromatograph (Water Associates) using a Macherey-Nagel C-18 column at 50° C. at a flow rate of 1 ml/min. The following elution solvent profile was used: Solvent A: 10% methanol/90% water; solvent B: 95% methanol, 5% diethylether. Initial conditions: 55% solvent B, then the amount of solvent B was increased to 65% over 10 minutes (linear), then to 67% B over 10 minutes (linear), then to 100% B over 2 minutes (curve 9) and held at 100% B for 10 minutes. Fractions were collected every 0.4 minutes and the radioactivity in each fraction was analyzed by liquid scintillation counting. The identity of the metabolites was established by co-chromatography with authentic standards obtained from the National Cancer Institute Chemical Carcinogen Repository.

Figure 13:
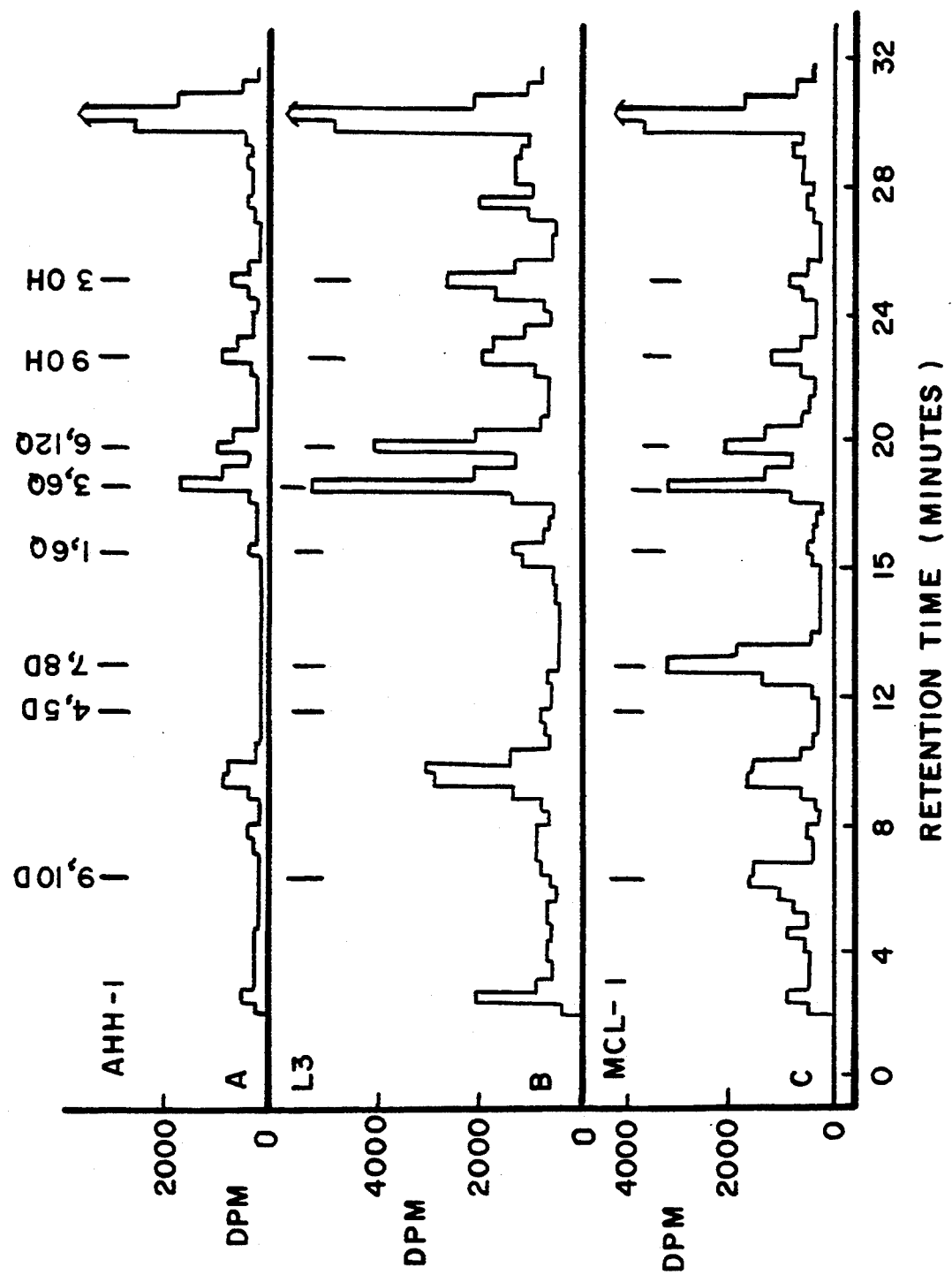
FIG. 13 is a graph showing the benzo(a)pyrene metabolite profile for the MCL-1 (FIG. 13C), L3 (FIG. 13B) and AHH-1 (FIG. 13A) cell lines.

The benzo(a)pyrene metabolite profile for the three cell lines is presented in FIG. 13. AHH-1 tk± cells were found to produce relatively low levels of metabolites which co-chromatographed with 3-hydroxy-benzo(a)pyrene (3 OH), 9-hydroxybenzo(a)pyrene (9 OH), benzo(a)pyrene-1,6-dione (1,6 Q), benzo(a)-pyrene-3,6-dione (3,6 Q) and benzo(a)pyrene-6,12-dione (6,12 Q). Also, an unidentified peak with a retention time of 10 minutes was observed. L3 cells produced qualitatively the same metabolite profile as AHH-1 tk± cells, however 2 to 3 times more of each metabolite was present. This observation is consistent with the higher levels of native P450IA1 activity in L3 cells. MCL-1 cells produce a qualitatively different metabolite profile from L3 or AHH-1 tk± cells. In particular, benzo(a)pyrene-9,10-dihydrodiol (9,10 D) and benzo(a)pyrene-7,8-dihydrodiol (7,8 D) were observed in MCL-1 cell incubations. The presence of these two metabolites is indicative of functional epoxide hydrolase activity. The overall level of metabolism in MCL-1 cells was comparable to L3 cells.

(b) MCL-1 Cell Line: Toxicity and Mutagenicity of Benzo(a)pyrene

The toxicity and mutagenicity of the carcinogen benzo(a)pyrene was determined using the procedures described above. Benzo(a)-pyrene is known to be metabolized by the P450IA1 to mutagenic species. This mutagenicity can be further potentiated by the action of epoxide hydrolase in concert with the P450IA1 to generate a vicinal diol-epoxide.

Figure 14:
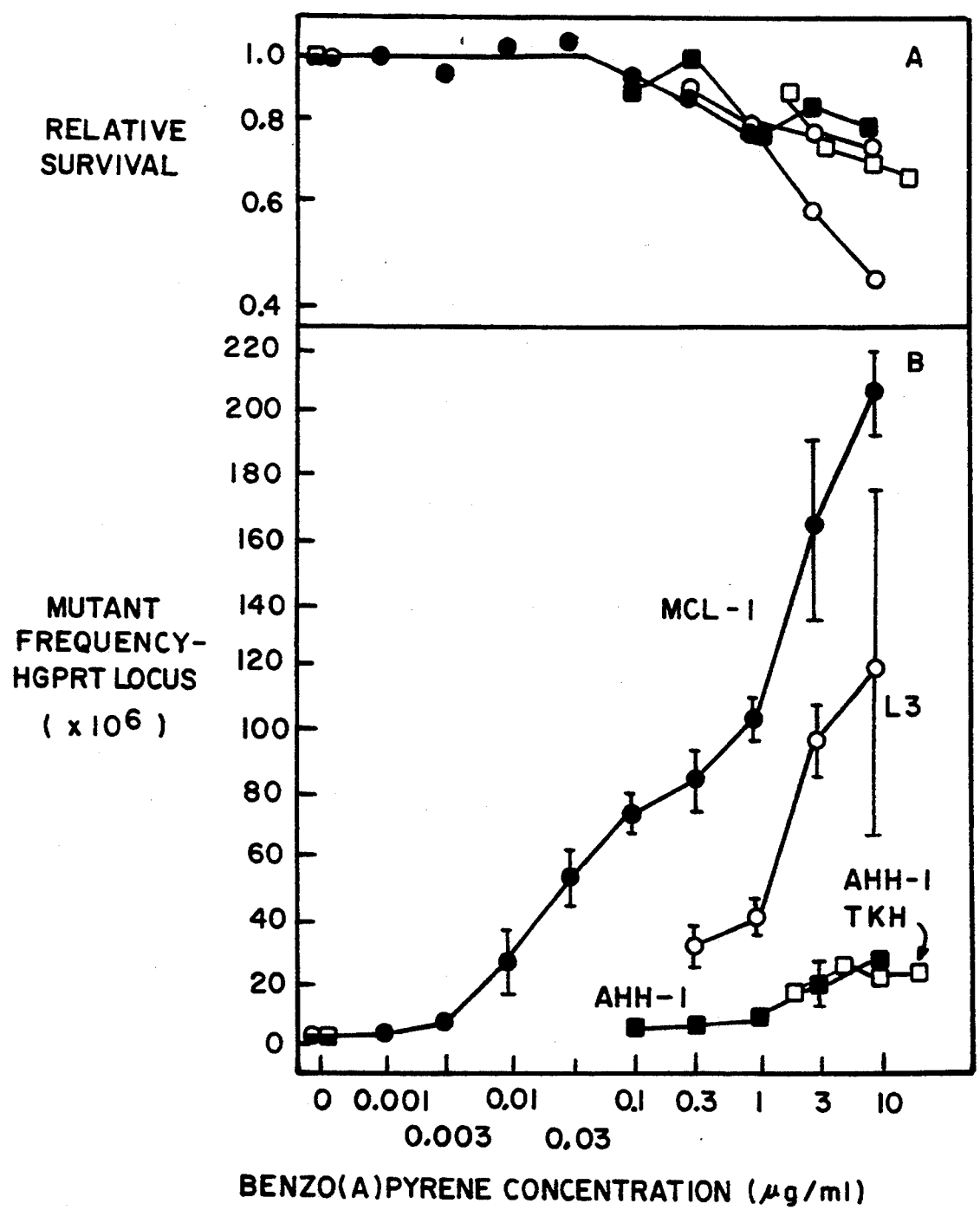
FIG. 14 is a graph showing the relative survival (FIG. 14A) and sensitivity (FIG. 14B) of the cell lines MCL-1, L3, AHH-1 tk± and AHH-1 to the mutagenic effects of benzo(a)pyrene.

Benzo(a)pyrene cytotoxicity and mutagenicity was determined in AHH-1 tk± cells, L3 cells and MCL-1 cells (FIG. 14). Mutagenicity was determined by measuring the increase in the 6-thioguanine (6TG) resistant fraction in cultures after mutagen exposure and phenotypic expression. Negative control values were the same for all three cell lines (approximately $4 \times 10^{-6}$). Cultures of AHH-1 tk± cells (open squares) treated with 2 to 20 ug/ml benzo(a)pyrene had mutant fractions, ranging from 15 to $20 \times 10^{-6}$. The magnitude of the benzo(a)pyrene-induced response observed for AHH-1 tk± cells was similar to the response of AHH-1 cells which has been previously published. These published data have been drawn on FIG. 14 (closed squares) for the purposes of comparison.

Cultures of L3 cells (open circles) treated with 0.3 to 10 ug/ml benzo(a)pyrene had a concentration dependent increase in mutant fractions ranging from 25 to $116 \times 10^{-6}$. Cultures of MCL-1 cells (closed circles) treated with 0.001 to 10 ug/ml benzo(a)pyrene also exhibited a concentration dependent increase in mutant fractions, ranging from 4 to $204 \times 10^{-6}$. Thus L3 cells are about five times more sensitive to the mutagenicity of benzo(a)pyrene than AHH-1 tk± cells and MCL-1 cells are about ten times more sensitive than AHH-tk±. These increases in sensitivity are consistent with the changes in metabolic capacity reported above.

MCL-1 cells were also found to be slightly more sensitive either than L3 cells or AHH-1 tk± cells to the cytotoxic effects of benzo(a)pyrene.

(c) MCL-1 Cell Line: Toxicity and Mutagenicity of Diethylnitrosamine

The toxicity and mutagenicity of the carcinogen diethylnitrosamine was determined using the procedures described above. Diethylnitrosamine is believed to be inefficiently metabolized to mutagenic species by the P450IA1. Diethylnitrosamine was tested with the MCL-1 cell line which expresses P450IIA2.

Figure 15:
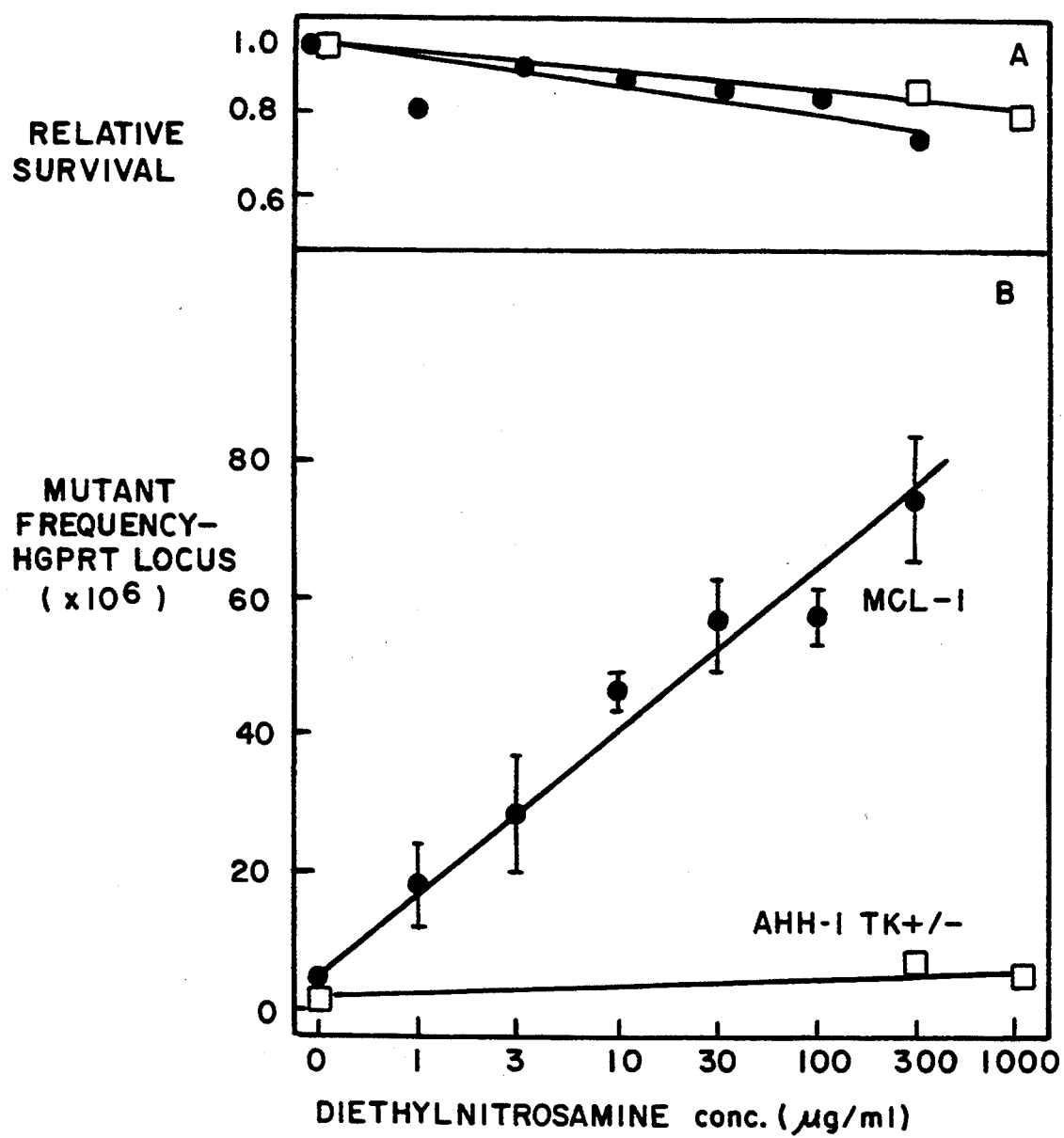
FIG. 15 is a graph comparing the relative survival (FIG. 15A) and sensitivity (FIG. 15B) of the MCL-1 cell line and AHH-1 tk± cell line to the mutagenic effects of diethylnitrosamine.

Diethylnitrosamine cytotoxicity and mutagenicity was determined in AHH-1 tk± cells and MCL-1 cells (FIG. 15). Mutagenicity was determined by measuring the 6-thioguanine (6TG) resistant fraction. The negative control values were the same for both cell lines (approximately $3 \times 10^{-6}$). No significant increase in the mutant fraction was observed of AHH-1 tk± cell cultures treated with up to 1000 ug/ml diethylnitrosamine (open squares). In contrast, a significant increase in the mutant fraction was observed in MCL-1 cells treated with as little as 1 ug/ml diethylnitrosamine (closed squares).

This increase was concentration-dependent, ranging from $18 \times 10^{-6}$ at 1 ug/ml to $75 \times 10^{-6}$ at 300 ug/ml.

Diethylnitrosamine was only slightly cytotoxic to either AHH-1 tk± cells and MCL-1 cells. No substantial difference in sensitivity to the cytotoxic effects of diethylnitrosamine was observed between the two cells lines.

(d) MCL-1 Cell Line: Toxicity and Mutagenicity of Dimethylnitrosamine

The toxicity and mutagenicity of the carcinogen dimethylnitrosamine was determined using the procedures described above. Dimethylnitrosamine, like diethylnitrosamine, is believed to be inefficiently metabolized to a mutagenic species by the P450IA1. Again, dimethylnitrosamine was tested with the MCL-1 cell line which expresses the P450IIA2.

Figure 16:
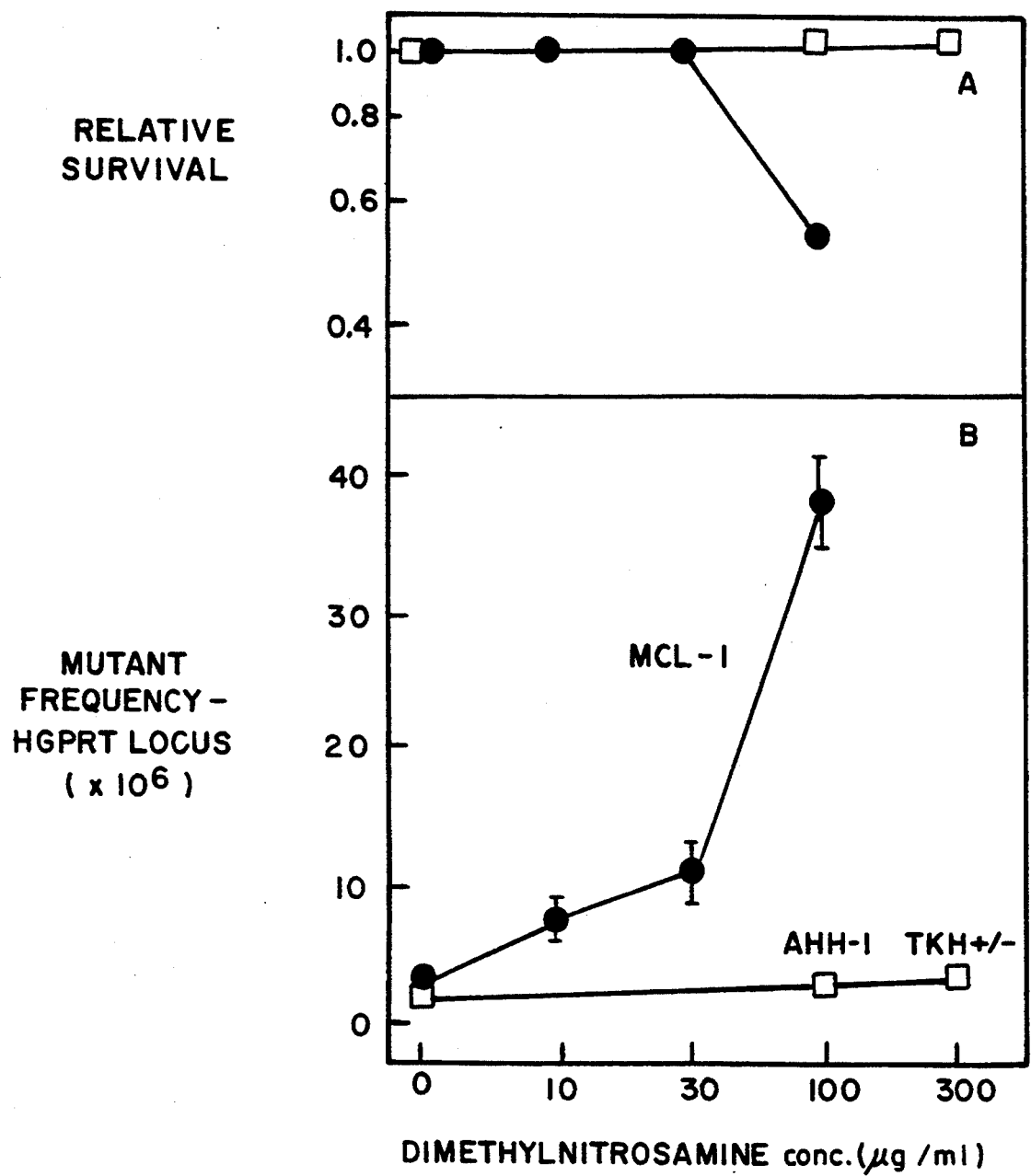
FIG. 16 is a graph comparing the relative survival (FIG. 16A) and sensitivity (FIG. 16B) of the MCL-1 cell line and AHH-1 tk± cell line to the mutagenic effects of dimethylnitrosamine.

Dimethylnitrosamine cytotoxicity and mutagenicity was determined in AHH-1 tk± cells (open squares) and MCL-1 cells (closed circles). AHH-1 tk± cells and MCL-1 cells had similar negative control mutant fractions (approximately $3 \times 10^{-6}$) (FIG. 16). Dimethylnitrosamine was essentially non-mutagenic to the AHH-1 tk± cell line at concentrations up to 300 ug/ml. In contrast, 10 ug/ml dimethylnitrosamine induced a significant mutagenic response in MCL-1 cells. The mutagenic response was concentration-dependent; 100 ug/ml dimethylnitrosamine induced a mutant fraction of $36 \times 10^{-6}$.

Dimethylnitrosamine cytotoxicity also was determined in AHH-1 tk± cells and MCL-1 cells. Dimethylnitrosamine was essentially non-cytotoxic to the AHH-1 tk± cell line. It was, however, cytotoxic to the MCL-1 cell line.

(e) MCL-1 Cell Line: Toxicity and Mutagenicity of Aflatoxin-$B_1$ at the tk and hgprt Loci The toxicity and mutagenicity of the carcinogen aflatoxin-$B_1$ was examined using the procedures described above. Aflatoxin-$B_1$ is metabolized by a several cytochrome P450 enzymes including the P450IA1 and potentially P450IIA2. Therefore it was anticipated that MCL-1 cells would be more sensitive to Aflatoxin-$B_1$ induced mutagenicity.

Figure 17:
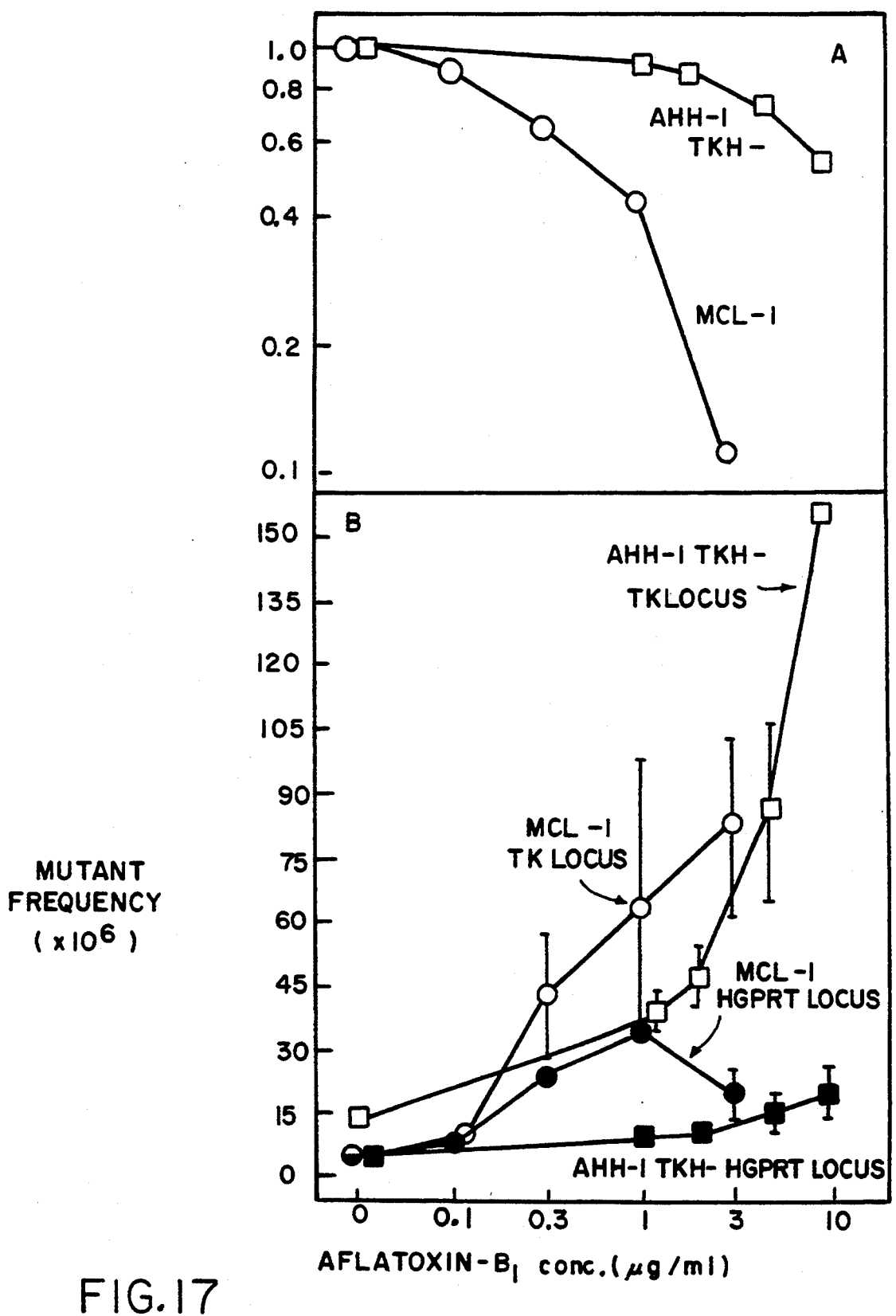
FIG. 17 is a graph comparing the relative survival (FIG. 17A) and sensitivity (FIG. 17B) of MCL-1 cell line and AHH-1 tk± cell line to the mutagenic effects of aflatoxin-$B_1$.

Aflatoxin-$B_1$ was found to be more cytotoxic to the MCL-1 cell line than the AHH-1 tk± cell line (FIG. 17). Treatment with 3 ug/ml Aflatoxin-$B_1$ reduced survival relative to untreated control cultures to 0.11 in MCL-1 cells while treatment of AHH-1 tk± cells with up to 10 ug/ml Aflatoxin-$B_1$ reduced the relative survival to 0.52.

Aflatoxin-$B_1$ was found to be mutagenic to both the MCL-1 cell line and the AHH-1 tk± cell line. Mutant frequency was measured at both the tk and hgprt loci in both cell lines. MCL-1 cells and AHH-1 tk± cells had comparable negative control mutant frequencies at the hgprt locus (approximately $4 \times 10^{-6}$). However, MCL-1 cells had a lower control mutant frequency at the tk locus than AHH-1 tk± cells ($5 \times 10^{-6}$ in MCL-1 cells versus $13.5 \times 10^{-6}$ in AHH-1 tk± cells). Aflatoxin-$B_1$ induced a concentration-dependent increase in mutant frequency in both cell lines and gene loci Cultures of AHH-1 tk± cell treated with 1 to 10 ug/ml Aflatoxin-$B_1$ had mutant frequencies of 8 to $18 \times 10^{-6}$ and 38 to $154 \times 10^{-6}$ at the hgprt (closed squares) and tk (open squares) loci respectively. Cultures of MCL-1 cells treated with 0.1 to 3 ug/ml Aflatoxin-$B_1$ had mutant frequencies of 6 to $34 \times 10^{-6}$ and 9 to $81 \times 10^{-6}$ at the hgprt (closed circles) and tk (open circles) loci respectively. When mutant frequencies at the hgprt locus were compared, MCL-1 cells were found to be more sensitive than AHH-1 cells to the mutagenic effects of Aflatoxin-$B_1$. When mutant frequencies at the tk locus were compared no significant difference between the two cell lines was observed. This observation is discussed below.

Figure 18:
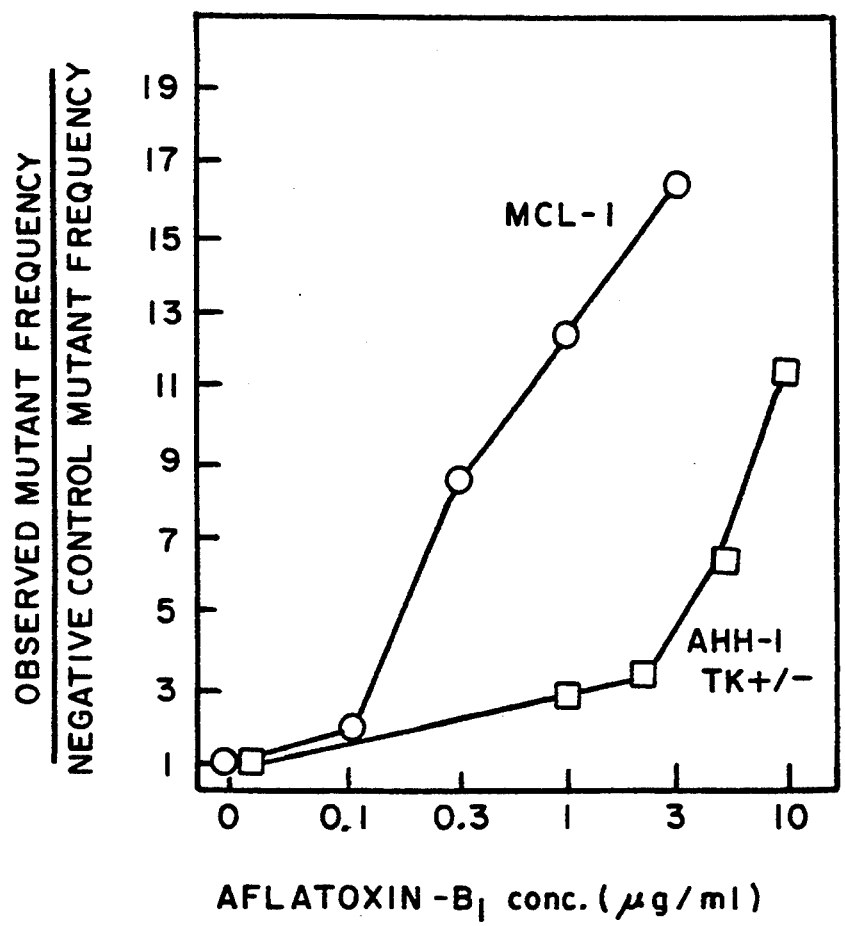
FIG. 18 is a graph showing the data of FIG. 17, but controlling for background activity.

The property of a lower negative control mutant frequency at the tk locus in the MCL-1 cell line (as compared to the AHH-1 tk± cell line) was associated with the isolation of the L3 cell line. Assays with lower negative control values have the potential to be statistically more sensitive to mutation induction. Therefore we compared a different measure of sensitivity to the data in FIG. 17 the signal to noise ratio derived by dividing the observed mutant frequency by the negative control mutant frequency, between the MCL-1 (open circles) and AHH-1 tk± cell lines (open squares) (FIG. 18). When this measure is compared, MCL-1 cells, by virtue of a lower negative control mutant frequency, were found to be approximately 4 times more sensitive to the mutagenicity of Aflatoxin-$B_1$.

This example demonstrates that MCL-1 cells are more sensitive to aflatoxin-$B_1$ induced mutagenicity and the tk locus in this cell line can be used to measure the induction of mutation.

It should be noted that our understanding of human procarcinogen activation and the P450 forms responsible for this activation is still in its infancy. Therefore, it is reasonable to expect that additional P450s may be established to have primary responsibility for the activation of other procarcinogens. The development of the MCL-1 and MCL-5 cell lines establishes the feasibility of transfecting multiple human P450 cDNAs and it is reasonable to expect that additional P450s could be incorporated into the MCL-1 or MCL-5 cells either in the same vectors or in an independently selected vector. Alternatively, a second cell line expressing a different set of P450 cDNAs could be developed.

One object of the invention was to construct a cell line expressing multiple P450 cDNAs and not to reconstruct the specific P450 profile of a particular tissue (i.e. liver). Accordingly, these results should not be interpreted as indicative of quantitative human tissue susceptabilty to procarcinogen exposure. However, as more is learned about specific P450 profiles in particular tissues, this study establishes that in principle it should be possible to reconstruct such a profile in a stable cell line for controlled analyses.

It should be understood that various changes and modifications of the preferred embodiments may be made within the scope of this invention. For example, other human cell lines or mammalian cell lines may be used to receive the recombinant expression vectors of the invention. Likewise, the methods of the invention may be used in connection with cloning human cytochrome P450 cDNA other than those described herein. Thus, it is intended that all matter contained in the above description shall be interpreted in an illustrative and not limiting sense.

REFERENCES

1. See, e.g., A. W. Hsie et al "The Dose-Response Relationship for Ethyl Methane Sulfanate-Induced Mutations of the HGPRT Locus and Chinese Hamster Ovary Cells", *Somatic Cell Genetics*, 1: 247–261 (1975).
2. See, e.g., C. F. Arlett et al "Mutation to 8-azaguanine Resistance Induced by Gamma-Irradiation in a Chinese Hamster Cell Line", *Mutation Res.*, 13: 59–65 (1971).
3. See, e.g., W. G. Thilly et al "Gene-Locus Mutation Assays in Diploid Human Lymphoblast Lines", Page 331-364, Chemical Mutagens, Volume 6, F. J. de Ferres et al, Ed; Plenum Publishing Company, New York (1980).
4. McCann, J., et al (1975) *Proc. Natl. Acad. Sci. USA* 72: 5135-5139.
5. Skopek, T. R. et al (1978) *Proc. Natl. Acad Sci. USA* 75: 410-414.
6. Hoffmann, G. R. et al (1975) *Mutat. Res.* 27: 307-318.
7. Chu E. H. Y. et al *Proc. Natl. Acad. Sci. USA* 61: 1306-1312.
8. Hsie, A. W., et al (1975) *Somat. Cell Genet.* 1: 383-389.
9. Clive, D. et al (1975) *Mutat. Res.* 31: 17-29.
10. Penman, B. W. et al (1976) *Somat. Cell Genet.* 2: 325-330.
11. Thilly, W. G. (1978), U.S. Pat. No. 4,066,510.
12. Skopek, T. R., et al (1981) U.S. Pat. No. 4,302,535.
13. Crespi, C. L. et al (1985) U.S. Pat. No. 4,532,204.
14. Ames, B. N. et al (1973) *Proc. Natl. Acad. Sci. USA* 70: 2281-2285.
15. Krahn, D. M. et al (1974) *Mutat. Res.* 46: 27-44.
16. Seikirk, J. K (1977) *Nature* (London) 270: 604-607.
17. Marguardt, H. et al (1972) *Cancer Res.* 32: 721-725.
18. Huberman, E. et al (1974) *Cancer Res.* 13: 326-333.
19. Battula, N. et al (1987) *Proc. Natl. Acad. Sci. USA* 84: 4073-4077.
20. Yoakum, G. H. (1984) *Biotechniques* ½, 24-30
21. Furth et al (1981) *Anal. Biochem.* 110: 1-8.
22. Young, R. A. et al (1983) *Proc. Natl. Acad. Sci. USA* 80: 1194-1198.
23. Young, R. A. et al (1983) *Science* 222: 778-782.
24. Sugden, B. et al (1985) *Mol. Cell Biol.* 5: 410-413.
25. Boyer, H. W. et al (1969) *J. Mol. Biol.* 41: 459-472.
26. Davies, R. L., Rudo, K., Turner, T. R. and Langenbach, R. (1989) *Carcinogensis* 10: 885-891.
27. Crespi, C. L., Langenbach, R. and Penman, B. W. (1990) *Progress in Clinical and Biological Research.* Mendelsohn, M. L. and Albertini, F. J. (eds) Wiley-Liss, New York, Vol. 340B, pp 97-106.
28. Phillips, I. R. et al (1985) *Proc. Natl. Acad. Sci. USA* 82: 983-987.
29. Davis et al (1980) *Advanced Bacterial Genetics* (Cold Spring Harbor Laboratory, Cold Spring Harbor, N.Y.).
30. Maniatis. T. et al (1982) *Molecular Cloning* (Cold Spring Harbor Laboratory, Cold Spring Harbor, N.Y.).
31. Denhardt, D. T. (1966) *Biochem. Biophys. Res. Commun.*, 28: 641-651.
32. Southern, E. M. (1975) *J. Mol. Biol.* 98: 503-517.
33. Bolivar, F. et al (1977) *Gene* 2: 95-113.
34. Garger, S. J. et al (1983) *Biochem. Biophys. Res. Commun.* 117: 835-832.
35. Gonzalez, F. J. et al (1981) *J. Biol. Chem.* 256: 4697-4700.
36. McKnight, S. L. (1980) *Nucl. Acids Res.* 8: 5931-5948.
37. Crespi, C. L., Steimel, D. T., Aoyama, T., Gelboin, H. V. and Gonzalez, F. J. (1990) *Mol. Carcinogenesis* 3: 5-8.
38. Gonzalez, F. J., Schmid, B. J., Umeno, M., McBride, O. W., Hardwick, J. P., Meyer, U. A., Gelboin, H. V. and Idle, J. R. (1988) Human P450PCN1: sequence, chromosome, localization, and direct evidence through cDNA expression that P450PCN1 is nifedipine oxidase. *DNA* 7: 79-86.
39. Davies, R. L., Crespi, C. L., Rudo, K., Turner, T. R. and Langenbach, R. (1989) Development of a human cell line by selection and drug-metabolizing gene transfection with increased capacity to activate promutagens. *Carcinogenesis* 10: 885-891.
40. Song B. J., Gelboin, H. V., Park, S.-S., Yang, C. S. and Gonzalez, F. J. (1986) *J. Biol. Chem.* 261: 16689-16697.
41. McKnight, S. L. (1980) *Nucl. Acids Res.* 8: 5949-5964.
42. Wagner et al (1981) *Proc. Natl. Acad. Sci. USA* 78: 1441-1445.
43. Crespi, C. L., Langenbach, R. and Penman, B. W. (1989) The development of a panel of human cell lines expressing specific human cytochrome P450 cDNAs. In: *Mutation and the Environment*, Mendelsohn, M. L. and Albertini, R. (Eds.) Alan Liss, New York, Vol. 340D, pp 97-106.
44. Greenlee, W. F. and Poland, A. (1978) *J. Pharmacol. Exp. Ther.* 205: 596-605.
45. Glatt, H. Kaltenbach, E. and Oesch, F. (1980) *Cancer Res.* 40: 2552-2556.
46. Burke, M. D. and Mayer, F. T. (1974) *Drug Metab. Disp.* 2: 583-588.
47. Crespi, D. L., Altman, J. D. and Marletta, M. A. (1985) *Chem. Biol. Interact* 53: 257-272.
48. Guenthner, T. M., Negishi, M. and Nebert, D. W. (1979) *Anal. Biochem.* 96: 201-207.
49. Peters, R., Bocher, R., Peaune, P., Iwasaki, M. and Gueugerich, F. P. (1990) In: Drugs, Metabolizing Enzymes: Genetics, Regulation and Toxicology. Ingelman-Sundberg, M. Gustafsson, J-A., and Orrenius, S. (eds). Proceedings of the VIIIth international symposium on Microsomes and Drug oxidations, Stockholm, Karolinska Institute, 1990, Pg. 234.
50. Waxman, D. J., Ko, A. and Walsh, C. (1983) *J. Biol. Chem.* 258: 11937-11943.
51. Penman, B. W. and Crespi, C. L. (1987) *Environ. Mol. Mutagen* 10: 35-60.
52. Crespi, C. L., Penman, B. W., Leakey, J. A. E., Arlotto, M. P., Stark, A., Parkinson, A., Turner, T., Steimel, D. T., Rudo, K., Davies, R. L. and Langenbach, R. (1990) Carcinogenesis 11: 1293-1300.
53. Penman, B. W., Crespi, C. L., Komives, E. A., Liber, H. L. and Thilly, W. G. (1983) *Mutat. Res.* 108: 417-436.
54. Crespi, C. L., Seixas, G. M., Turner, T. and Penman, B. W. (1990) *Environ. Molec. Mutagen.* 15: 71-77.
55. Shimada, T. Mazrtin, M. V., Pruess-Schwartz, D. Marnett, L. and Guengerich, F. P. (1989) *Cancer Res.* 49: 6304-6312.
56. McManus, M. E., Burgess, W. M., Veronese, M. E., Huggett, A., Quattrochi, L. C., and Tukey, R. H. (1990) *Cancer Res.* 50: 3367-3376.

What is claimed is:
1. A culture consisting essentially of the human cell line MCL-5 having ATCC accession number CRL 10575.
2. A cell culture consisting of the human cell line MCL-5 having ATCC Accession No. CRL 10575.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

CCCCAGTCCC CGCCTTGAAT                                                        20

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GCAGCTGGAA TCTGCCCC                                                          18

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

ACATTGGAGA ATGTGCGGAT                                                        20

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

TCGAGATGTC TGCCG                                                                 15

( 2 ) INFORMATION FOR SEQ ID NO:5:

( i ) SEQUENCE CHARACTERISTICS:
    ( A ) LENGTH: 11 base pairs
    ( B ) TYPE: nucleic acid
    ( C ) STRANDEDNESS: both
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CGGCAGACAT C                    11